US009206384B2

(12) United States Patent
Lee et al.

(10) Patent No.: US 9,206,384 B2
(45) Date of Patent: Dec. 8, 2015

(54) MICRO-INCUBATION SYSTEMS FOR MICROFLUIDIC CELL CULTURE AND METHODS

(71) Applicant: EMD Millipore Corporation, Billerica, MA (US)

(72) Inventors: Philip J. Lee, Alameda, CA (US); Terry Gaige, Hayward, CA (US); Wei Hsuan (Jessie) Ho, Foster City, CA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/692,869

(22) Filed: Dec. 3, 2012

(65) Prior Publication Data

US 2013/0171679 A1    Jul. 4, 2013

Related U.S. Application Data

(60) Provisional application No. 61/566,651, filed on Dec. 3, 2011.

(51) Int. Cl.
| C12M 1/12 | (2006.01) |
| C12M 1/00 | (2006.01) |
| C12M 3/06 | (2006.01) |
| C12Q 1/02 | (2006.01) |

(Continued)

(52) U.S. Cl.
CPC .............. *C12M 29/24* (2013.01); *B01L 3/563* (2013.01); *C12M 23/16* (2013.01); *C12M 23/40* (2013.01); *C12M 29/10* (2013.01); *C12M 41/14* (2013.01); *C12M 41/34* (2013.01); *C12M 41/36* (2013.01); *C12Q 1/02* (2013.01)

(58) Field of Classification Search
CPC ...... C12M 23/40; C12M 23/16; C12M 29/04; C12M 23/34; C12M 25/02; C12M 23/24; C12M 23/08; C12M 41/14; C12M 23/48; C12Q 1/02; B01L 17/52; B01L 17/00; B01L 2300/0829
USPC .......................................... 435/297.2, 303.1
See application file for complete search history.

(56) References Cited

U.S. PATENT DOCUMENTS

| 4,055,613 A | 10/1977 | Kapral |
| 4,661,455 A | 4/1987 | Hubbard |
| 4,734,373 A | 3/1988 | Bartal |

(Continued)

FOREIGN PATENT DOCUMENTS

| DE | 19948087 A1 | 5/2001 |
| EP | 0155237 A2 | 9/1985 |

(Continued)

OTHER PUBLICATIONS

Optics Express, vol. 14, No. 13, Jun. 2006, pp. 6253-6256, "Fabrication of polymer microlens arrays using capillary forming with a soft mold of micro-holes array and UV-curable polymer", Chang, et al.

(Continued)

*Primary Examiner* — Michael Hobbs
(74) *Attorney, Agent, or Firm* — Nields, Lemack & Frame, LLC

(57) ABSTRACT

A micro-incubator manifold for improved microfluidic configurations and systems and methods of manufacture and operation for a manifold and automated microfluidic systems.

16 Claims, 26 Drawing Sheets

(51) Int. Cl.
  *C12M 1/34* (2006.01)
  *B01L 3/00* (2006.01)

(56) References Cited

U.S. PATENT DOCUMENTS

| | | |
|---|---|---|
| 4,748,124 A | 5/1988 | Vogler |
| 5,079,168 A | 1/1992 | Amiot |
| 5,153,131 A | 10/1992 | Wolf et al. |
| 5,310,676 A | 5/1994 | Johansson et al. |
| 5,330,908 A | 7/1994 | Spaulding |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wolf et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem et al. |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Dapprich |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 2002/0039785 A1 | 4/2002 | Schroeder et al. |
| 2002/0108860 A1 | 8/2002 | Staats |
| 2002/0108868 A1 | 8/2002 | Fairbourn et al. |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim et al. |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom et al. |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Burd Mehta et al. |
| 2004/0132175 A1 | 7/2004 | Vetillard et al. |
| 2004/0202579 A1 | 10/2004 | Larsson et al. |
| 2004/0229349 A1 | 11/2004 | Daridon |
| 2004/0238484 A1 | 12/2004 | Le Pioufle et al. |
| 2005/0009179 A1 | 1/2005 | Gemmiti et al. |
| 2005/0019213 A1 | 1/2005 | Kechagia et al. |
| 2005/0032208 A1 | 2/2005 | Oh et al. |
| 2005/0072946 A1 | 4/2005 | Studer et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2005/0266582 A1 | 12/2005 | Modlin et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 | 5/2007 | Strand et al. |
| 2007/0128715 A1 | 6/2007 | Vukasinovic et al. |
| 2007/0264705 A1 | 11/2007 | Dodgson |
| 2007/0275455 A1 | 11/2007 | Hung et al. |
| 2008/0038713 A1 | 2/2008 | Gao et al. |

(56) References Cited

U.S. PATENT DOCUMENTS

| | | | |
|---|---|---|---|
| 2008/0085556 | A1 | 4/2008 | Graefing et al. |
| 2008/0176318 | A1 | 7/2008 | Wilson et al. |
| 2008/0194012 | A1 | 8/2008 | Lee et al. |
| 2008/0227176 | A1 | 9/2008 | Wilson |
| 2008/0233607 | A1 | 9/2008 | Yu et al. |
| 2009/0023608 | A1 | 1/2009 | Hung et al. |
| 2009/0123961 | A1 | 5/2009 | Meyvantsson et al. |
| 2009/0148933 | A1 | 6/2009 | Battrell et al. |
| 2009/0203126 | A1 | 8/2009 | Hung et al. |
| 2010/0151571 | A1 | 6/2010 | Vukasinovic et al. |
| 2010/0196908 | A1 | 8/2010 | Opalsky et al. |
| 2012/0003732 | A1 | 1/2012 | Hung et al. |
| 2012/0164036 | A1 | 6/2012 | Stern et al. |
| 2013/0059322 | A1 | 3/2013 | Hung et al. |
| 2013/0081757 | A1 | 4/2013 | Hung et al. |
| 2013/0090268 | A1 | 4/2013 | Hung et al. |
| 2013/0171682 | A1 | 7/2013 | Hung et al. |
| 2014/0057311 | A1 | 2/2014 | Kamm et al. |
| 2014/0090735 | A1 | 4/2014 | Hung et al. |
| 2014/0099705 | A1 | 4/2014 | Hung et al. |
| 2014/0287489 | A1 | 9/2014 | Lee et al. |

FOREIGN PATENT DOCUMENTS

| | | |
|---|---|---|
| EP | 0725134 A2 | 8/1996 |
| EP | 0890636 A1 | 1/1999 |
| GB | 1539263 | 1/1979 |
| WO | 91/15570 A1 | 10/1991 |
| WO | 00/56870 A1 | 9/2000 |
| WO | 00/60352 A1 | 10/2000 |
| WO | 00/78932 A1 | 12/2000 |
| WO | 01/92462 A1 | 12/2001 |
| WO | 03/085080 A1 | 10/2003 |
| WO | 03/098218 A1 | 11/2003 |
| WO | 2004/059299 A1 | 7/2004 |
| WO | 2004/106484 A2 | 12/2004 |
| WO | 2005/035728 A1 | 4/2005 |
| WO | 2007/008606 A1 | 1/2007 |
| WO | 2007/008609 A2 | 1/2007 |
| WO | 2009/089189 A2 | 7/2009 |
| WO | 2009/102453 A2 | 8/2009 |

OTHER PUBLICATIONS

Lab Chip, 2007, vol. 7, pp. 641-643, published by the Royal Society of Chemistry, "Rapid fabrication of microchannels using microscale plasma activated templating (uPLAT) generated water molds", Chao, et al.
J. Biochem., vol. 130, pp. 367-376, (2001), "A Method for Micrometer Resolution Patterning of Primary Culture Neurons for SPM Analysis", Degenaar, et al.
Lab Chip, 2003, vol. 3, pp. 318-323, published by the The Royal Society of Chemistry, "Fabrication of microfluidic mixers and artificial vasculatures using a high-brightness diode-pumped Nd: YAG laser direct write method", Lim, et al.
Angew. Chem. Int. Ed., 2004, vol. 43, pp. 1531-1536, "Minimal Functional Model of Hemostasis in a Biomimetic Microfluidic System", Runyon, et al.
Biomedical Microdevices, 2003, vol. 5, No. 3, pp. 235-244, "Microfluidic Patterning of Cellular Biopolymer Matrices for Biomimetic 3-D Structures", Tan, et al.
Lab on a Chip, 2007, vol. 7, pp. 763-769, "A hydrogel-based microfluidic device for the studies of directed cell migration", Cheng, et al.
Lab on a Chip, 2009, vol. 9, p. 1797-1800, "Selective and tunable gradient device for cell culture and chemotaxis study", Kim, et al.
Biomed Microdevices (2008), vol. 10, pp. 499-507, "Microfluidic switching system for analyzing chemotaxis responses of wortmannin-inhibited HL-60 cells", Liu, et al.
Lab on a Chip, 2007, vol. 7, pp. 1673-1680, "Gradient generation by an osmotic pump and the behavior of human mesenchymal stem cells under the fetal bovine serum concentration gradient", Park, et al.
Notice of Allowance mailed Jan. 13, 2014 in co-pending U.S. Appl. No. 13/602,328.
Notice of Allowance mailed Dec. 23, 2013 in co-pending U.S. Appl. No. 13/602,331.
Office Action mailed Dec. 31, 2013 in co-pending U.S. Appl. No. 13/761,130.
Extended European Search Report mailed Apr. 3, 2012 in European patent application No. EP 06786499.
International Search Report and Written Opinion mailed Apr. 9, 2009 in PCT application No. PCT/US06/26364 (corresponding to U.S. Appl. No. 11/994,997).
International Search Report and Written Opinion mailed Jul. 30, 2009 in PCT application No. PCT/US2009/030168.
Extended European Search report mailed Oct. 21, 2013 in European patent application No. EP 09701350.
International Search Report mailed May 14, 2013 in PCT application No. PCT/US2013/024999.
International Search Report mailed Mar. 19, 2013 in corresponding PCT application No. PCT/US2012/067632.
Cellasic Corporation, ONIX Application Note, "Microincubator for long term live cell microscopy", Feb. 3, 2012, pp. 1-4.
Lab Chip, 2005, vol. 5, No. 4, pp. 401-406, published by The Royal Society of Chemistry, "Human neural stem growth and differentiation in a gradient-generating microfluidic device", Chung, et al.
Biotechnology and Bioengineering, vol. 89, No. 1, Jan. 5, 2005, pp. 1-8, "Continuous Perfusion Microfluidic Cell Culture Array for High-Throughput Cell-Based Assays", Hung, et al.
Lab Chip, 2008, vol. 8, No. 1, pp. 34-57, published by The Royal Society of Chemistry, "Biomolecular gradients in cell culture systems", Keenan, et al.
Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.
Lab Chip, 2009, vol. 9, No. 1, pp. 164-166, published by The Royal Society of Chemistry, "Dynamic cell culture: a microfluidic function generator for live cell microscopy", Lee, et al.
Journal of the Association for Laboratory Automation (JALA), 2007, vol. 12, No. 6, pp. 363-367, "Microfluidic System for Automated Cell-Based Assays", Lee, et al.
Biomaterials, 2008, vol. 29, No. 22, pp. 3237-3244, "A gel-free 3D microfluidic cell culture system", Ong, et al.
Office Action mailed Apr. 25, 2013 in co-pending U.S. Appl. No. 13/602,328.
Notice of Allowance mailed Oct. 28, 2013 in co-pending U.S. Appl. No. 13/602,328.
Office Action mailed Jun. 17, 2010 in co-pending U.S. Appl. No. 12/019,857.
Final Rejection mailed Feb. 28, 2011 in co-pending U.S. Appl. No. 12/019,857.
Office Action mailed Sep. 15, 2011 in co-pending U.S. Appl. No. 12/019,857.
Final Rejection mailed May 31, 2012 in co-pending U.S. Appl. No. 12/019,857.
Office Action—Restriction—mailed Jul. 13, 2011 in co-pending U.S. Appl. No. 12/348,907.
Office Action mailed Dec. 23, 2011 in co-pending U.S. Appl. No. 12/348,907.
Final Rejection mailed Sep. 17, 2012 in co-pending U.S. Appl. No. 12/348,907.
Office Action Nov. 28, 2012 in co-pending U.S. Appl. No. 13/011,857.
Final Rejection mailed Aug. 14, 2013 in co-pending U.S. Appl. No. 13/011,857.
Office Action—Restriction—mailed Feb. 22, 2013 in co-pending U.S. Appl. No. 13/436,992.
Office Action mailed Sep. 6, 2013 in co-pending U.S. Appl. No. 13/436,992.
Office Action—Restriction—mailed Oct. 7, 2013 in co-pending U.S. Appl. No. 13/761,130.
Office Action—Restriction—mailed Mar. 9, 2011 in co-pending U.S. Appl. No. 11/994,997.
Office Action mailed Jul. 18, 2011 in co-pending U.S. Appl. No. 11/994,997.

(56) References Cited

OTHER PUBLICATIONS

Final Rejection mailed Feb. 8, 2012 in co-pending U.S. Appl. No. 11/994,997.
Office Action mailed Sep. 11, 2013 in co-pending U.S. Appl. No. 11/994,997.
Office Action mailed Feb. 22, 2013 in co-pending U.S. Appl. No. 13/602,331.
Notice of Allowance mailed Nov. 13, 2013 in co-pending U.S. Appl. No. 13/602,331.
Final Rejection mailed Apr. 11, 2014 in co-pending U.S. Appl. No. 13/436,992.
Final Rejection mailed Apr. 4, 2014 in co-pending U.S. Appl. No. 11/994,997.
Notice of Allowance mailed Dec. 22, 2014 in co-pending U.S. Appl. No. 12/348,907.
Office Action mailed Nov. 6, 2014 in co-pending U.S. Appl. No. 13/436,992.
Office Action mailed Oct. 27, 2014 in co-pending U.S. Appl. No. 13/761,130.
Final Rejection mailed Mar. 23, 2015 in co-pending U.S. Appl. No. 13/436,992.
Notice of Allowance mailed Apr. 27, 2015 in co-pending U.S. Appl. No. 12/019,857.
Office Action mailed May 13, 2015 in co-pending U.S. Appl. No. 14/053,688.
Notice of Allowance mailed May 6, 2015 in co-pending U.S. Appl. No. 13/761,130.
Notice of Allowance mailed May 4, 2015 in co-pending U.S. Appl. No. 14/081,314.
Office Action mailed Jun. 19, 2015 in corresponding U.S. Appl. No. 14/221,615.
Notice of Allowance mailed Jun. 22, 2015 in co-pending U.S. Appl. No. 11/994,997.
Office Action mailed Oct. 7, 2014 in co-pending U.S. Appl. No. 12/019,857.
Final Rejection mailed Oct. 20, 2014 in co-pending U.S. Appl. No. 13/011,857.
Office Action mailed Sep. 15, 2014 in co-pending U.S. Appl. No. 14/081,314.
Advisory Action mailed Jul. 24, 2014 in co-pending U.S. Appl. No. 11/994,997.
International Preliminary Report on Patentability mailed Jun. 12, 2014 in corresponding PCT application No. PCT/US2012/067632.
Engineering Aspects of Food Biotechnology, Chapter 5, CRC Press: Boca Raton, FL, 2004, copyright 2014, p. 127, "Meet the Stem Cells; Production of Cultured Meat from a Stem Cell Biology Perspective", Brinkhof, et al., 3 pages.
Office Action mailed May 13, 2014 in co-pending U.S. Appl. No. 13/011,857.
Final Rejection mailed Jun. 25, 2014 in co-pending U.S. Appl. No. 13/761,130.
Lab Chip, 2005, vol. 5, pp. 44-48, "A novel high aspect ratio microfluidic design to provide and stable and uniform microenvironment for cell growth in a high throughput mammalian cell culture array", Hung, et al.
Office Action mailed Jan. 26, 2015 in co-pending U.S. Appl. No. 11/994,997.
Notice of Allowance mailed Aug. 4, 2015 in co-pending U.S. Appl. No. 13/761,130.
Notice of Allowance mailed Aug. 24, 2015 in co-pending U.S. Appl. No. 14/081,314.
European communication dated Jul. 28, 2015 in corresponding European patent application No. 12852539.1.
Notice of Allowance mailed Oct. 13, 2015 in co-pending U.S. Appl. No. 12/348,907.
Office action mailed Oct. 6, 2015 in co-pending U.S. Appl. No. 13/011,857.
Notice of Allowance mailed Sep. 21, 2015 in co-pending U.S. Appl. No. 14/053,688.

Section A-A (Open State)
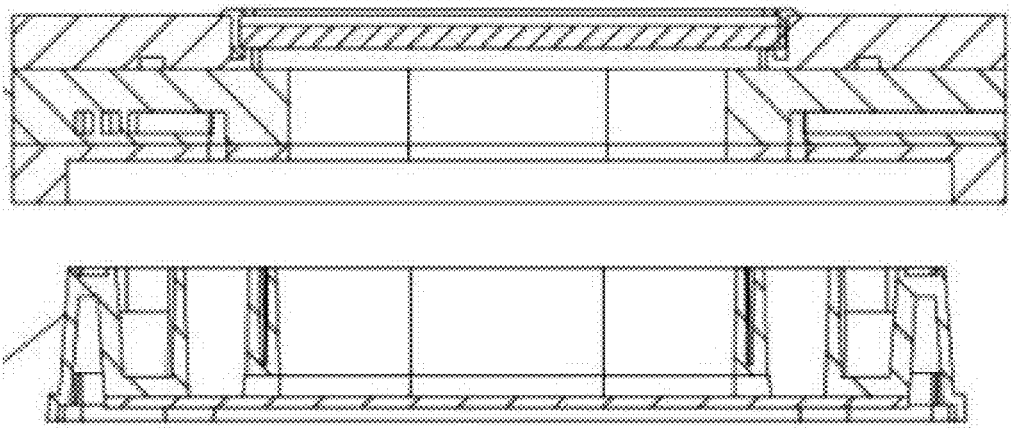
Section A-A (Sealed State)
Gas mixture in
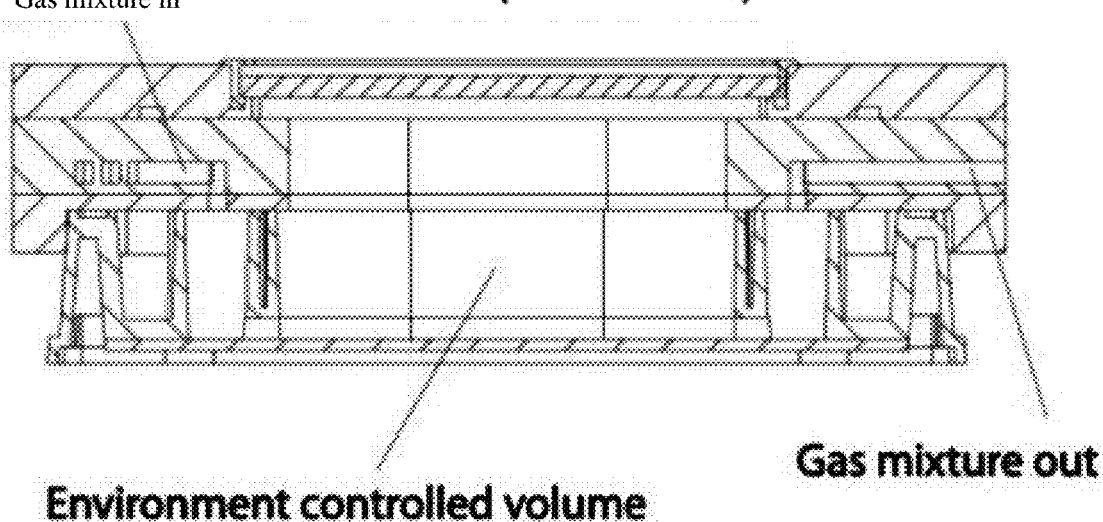
Environment controlled volume
Gas mixture out
*FIG. 7*

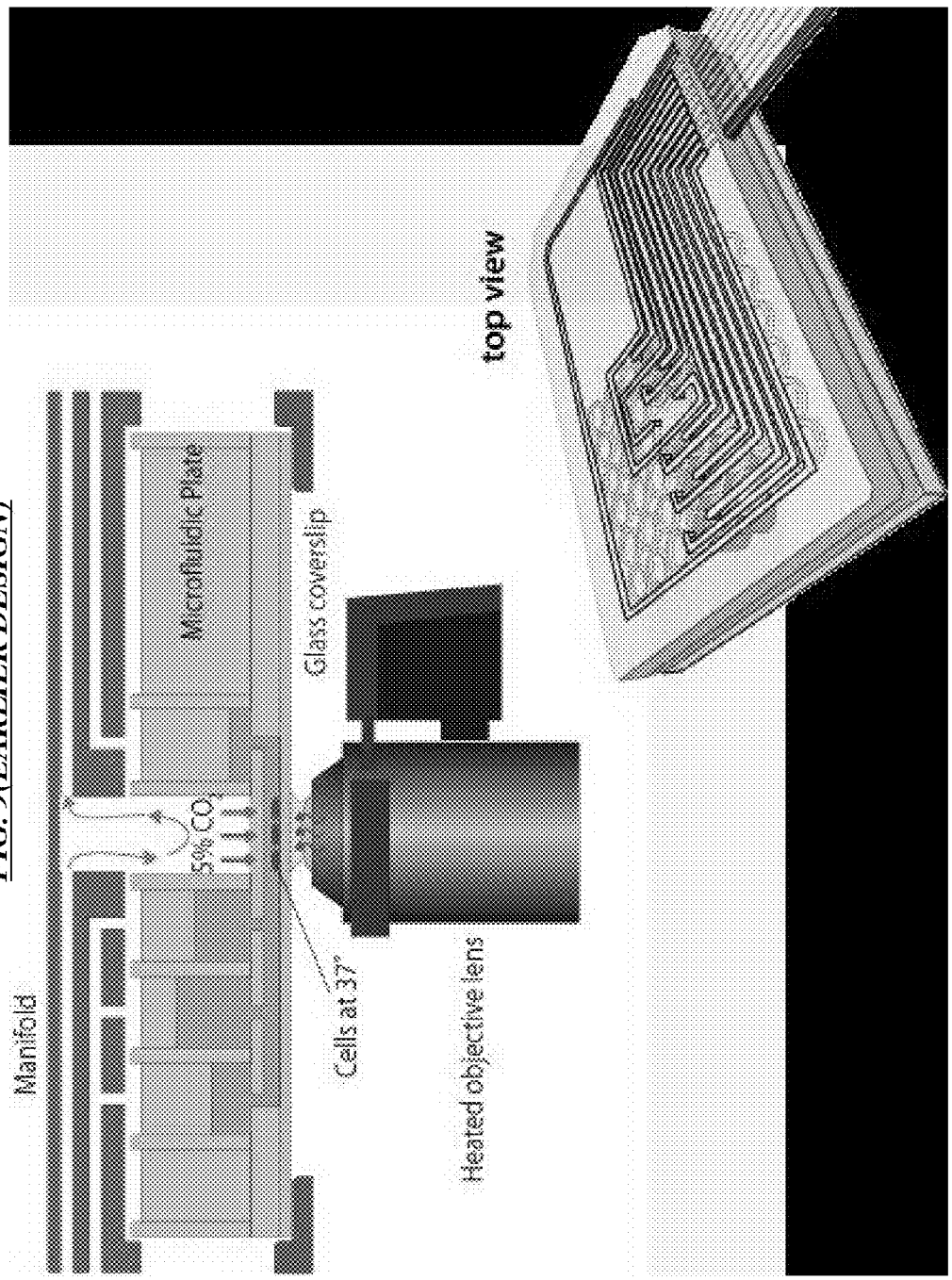
FIG. 9 (EARLIER DESIGN)

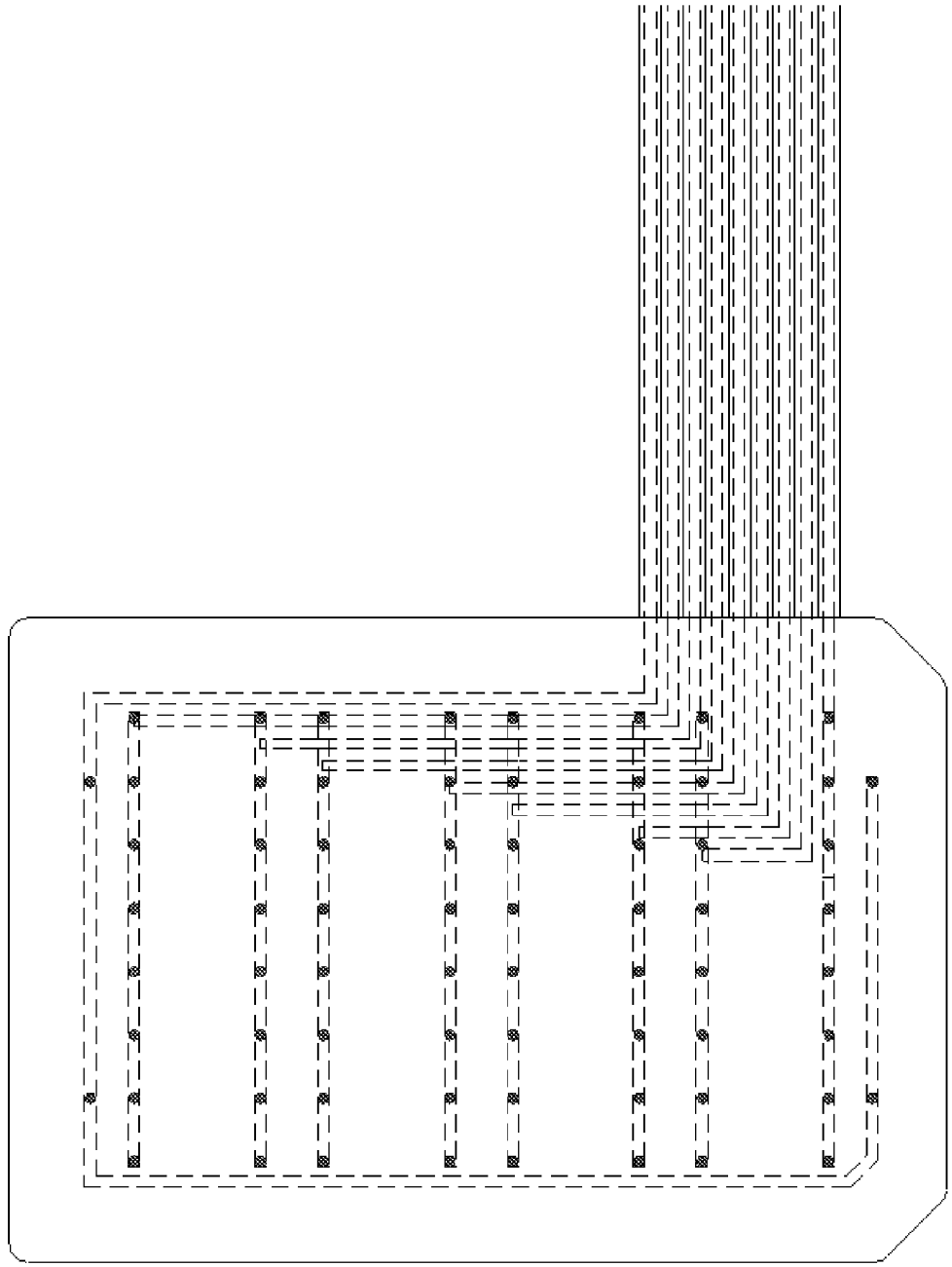
FIG. 10A (EARLIER DESIGN / PRIOR ART)

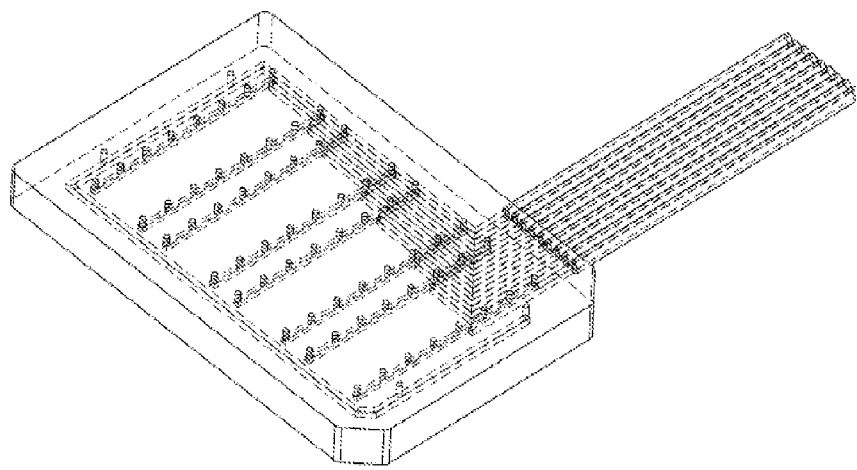
*FIG. 10B (EARLIER DESIGN / PRIOR ART)*
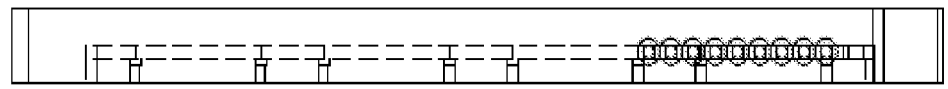
*FIG. 10C (EARLIER DESIGN / PRIOR ART)*

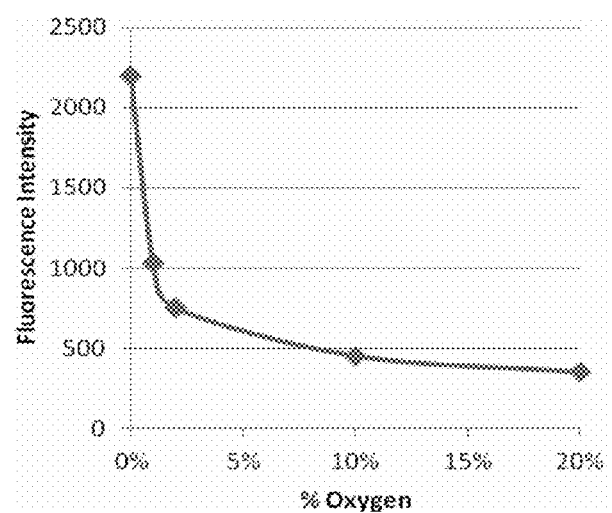
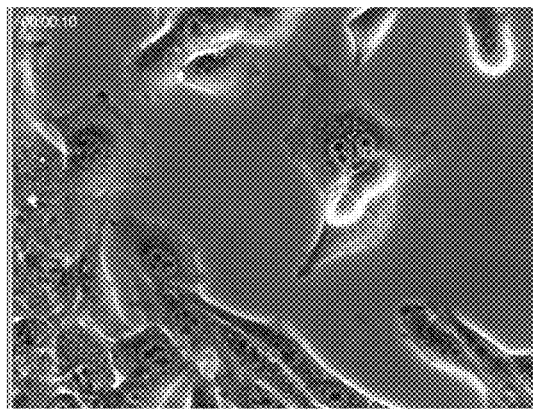
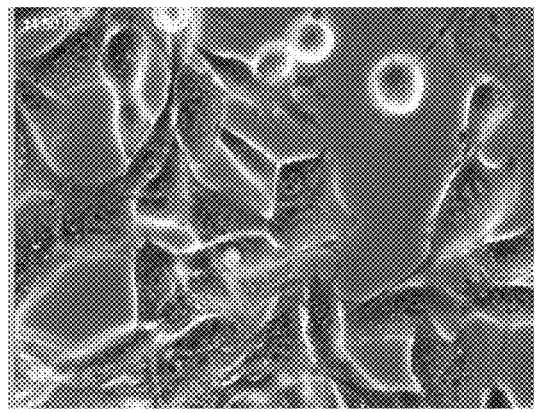
*FIG. 13*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 19. (TABLE 1)*

Appendix: Electrical Diagrams of the ONIX-MIC system

MICRO-INCUBATION SYSTEMS FOR MICROFLUIDIC CELL CULTURE AND METHODS

CROSS REFERENCE TO RELATED APPLICATIONS

This application claims benefit of priority from provisional patent application 61/566,651, filed Dec. 3, 2011, which is hereby incorporated by reference for all purposes.

This application incorporates each of the following provisional patent applications by reference:
  61/367,371 filed Jul. 23, 2010
  61/297,278 filed Jan. 21, 2010
  61/471,103 filed Apr. 1, 2011

This application is related to material discussed in one or more of the following applications, each of which are incorporated herein by reference for all purposes: U.S. Provisional Patent Application No. 61/037,297, filed Mar. 17, 2008; U.S. Provisional Patent Application No. 61/018,882, filed Jan. 3, 2008; U.S. patent application Ser. No. 11/994,997, filed Aug. 11, 2008, which is a National Stage Entry of PCT/US06/26364, filed Jul. 6, 2006 and which claims priority from U.S. Provisional Patent Application No. 60/773,467, filed Feb. 14, 2006 and from U.S. Provisional Patent Application No. 60/697,449, filed Jul. 7, 2005; U.S. patent application Ser. No. 12/019,857, filed Jan. 25, 2008, which claims priority to U.S. Provisional Patent Application No. 60/900,651 filed Feb. 8, 2007; U.S. patent application Ser. No. 11/648,207, filed Dec. 29, 2006, now issued as U.S. Pat. No. 8,257,964, which claims priority to U.S. Provisional Patent Application No. 60/756,399, filed Jan. 4, 2006; and U.S. patent application Ser. No. 12/348,907, filed Jan. 5, 2009.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in various embodiments relates to assays, systems, and/or devices for culturing cells or other biologic material in controlled environments and that are applicable to related fields generally using microfluidic systems. Particular embodiments involve configurations that can be used with various standard automated handling systems, with active or passive loading and perfusion of medium and to provide high-throughput multi-assay automated systems for culturing, viewing, and analyzing cell growth, invasion, movement, chemotaxis or other properties. More specifically, the invention relates in specific embodiments to heat control systems for microfluidic culture plates and other automated systems for culture plates.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Microfluidic cell culture is an important technology for applications in drug screening, tissue culturing, toxicity screening, and biologic research and can provide improved biological function, higher-quality cell-based data, reduced reagent consumption, and lower cost. High quality molecular and cellular sample preparations are important for various clinical, research, and other applications. In vitro samples that closely represent their in vivo characteristics can potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Numerous aspects related to microfluidic systems, devices, methods and manufacturing are discussed in the above-referenced and related patent applications. While no particular limitations should be read form those applications into any claims presented herein, these incorporated documents provide useful background material related to specific embodiments.

Other publications and/or patent documents that discuss various strategies related to cell culture using microfluidic systems and related activities include the following U.S. patent applications and non-patent literature, which, along with all citations therein, are incorporated herein by reference for all purposes. A listing of these references here does not indicate the references constitute prior art.

Cytoplex, Inc. U.S. Pat. No. 6,653,124 "Array-based microenvironment for cell culturing, cell monitoring and drug-target validation."

Cellomics, Inc. U.S. Pat. No. 6,548,263 "Miniaturized cell array methods and apparatus for cell-based screening."

Fluidigm, Inc. Published Application 20040229349 (Nov. 18, 2004) "Microfluidic particle-analysis systems."

Earlier work and patent applications as cited above, involving at least one of the present inventors, discuss various configurations, methods, and systems related to microfluidic cell culture and that work and those publications are is incorporated herein by reference.

SUMMARY

The present invention involves various components, systems, and methods related to improved microfluidic cell culture devices and systems, in particular systems for the culturing and/or analysis and/or viewing of cells under controlled temperature and gas parameters. In one aspect, the invention involves novel microfluidic cell culture devices, systems and methods that have advantages over previously proposed culture systems providing in some embodiments, more convenient and unobtrusive heating and gas control and also providing automatic handling. In another aspect, the invention involves novel structures and methods for integrating heating and gas control with multiple microfluidic cell culture units in various multi cell culture unit systems, such as to a microtiter well plate structure including various standard well plate formats (e.g., a 96-well SBS culture plate, or other plate formats, including plates having 6, 12, 24, 96, 384 or 1536 sample wells, as well as open bottom standard well plates, as well as plates with specific areas for cell culture and/or viewing.

Removable Multi-Chamber Plate Manifold with Gas and/or Temperature Control

In particular embodiments and examples, design features include providing a cell culture device in a convenient format that allows for the elimination of tubing and connectors to the plates themselves and provides temperature control and monitoring mostly or entirely contained in a removable manifold that fits onto the plates with a gas seal, thereby providing the ability to maintain long-term cell culture with temperature and/or gas control in a culture platform that maintains the ability to easily observe cells and that is easily removable from the culture plate. A system of the invention can be used with a variety of cell culture units on culture plates, such as those described in the above referenced patent applications, including cell culture units for determining cellular invasion, culture units with gel culture media, and a variety of other culture units as described herein or in incorporated related applications.

Living cells generally require careful control of their physical environment, including nutrient and gas exchange, temperature regulation, and protection from stress. Advanced micro-scale cell culture methods such as described in above referenced patent applications enable structural control (microfabrication), and perfusion control (microfluidics).

Micro-Incubation, and Micro-Incubator Chamber/Well in Contact Microfluidic Cell Culture Chambers According to specific embodiments, the present invention is directed to an additional area of this field, referred to at times herein as micro-incubation, to provide control of temperature and gas atmosphere for use in micro-scale cell culture systems in a way that is unobtrusive to observational equipment and that further is easily attached and removed from a culture plate in specific embodiments.

According to specific embodiments, the invention provides a miniaturization of the traditional cell culture incubator concept to perform dynamic, continuous temperature and gas regulation directly to a microfluidic chamber. In example implementations, this is possible through the creation of a micro-incubator chamber of about 5 mL volume in contact with the microfluidic cell culture chambers (1 ul). The temperature and gas content of the micro-incubator quickly transfers to the cell culture chamber (by conduction and diffusion). In specific embodiments, the micro-incubator is maintained by a novel manifold design as described herein. Manifolds according to specific embodiments of the invention can be controlled by various systems and software.

System for Time-Lapse Microscopy of Living Cells

Many products and methods enable time-lapse microscopy of living cells. Three approaches that are commonly known can generally be understood as: (1) full microscope enclosures, (2) stage-top incubators, and (3) perfusion chambers.

Full microscope enclosures surround the entire microscope except for some heat generating or heat sensitive components such as the camera and illumination sources. The air within the enclosure is circulated and maintained at the desired temperature and gas environment of the sample. An advantage of this method is that temperature control of the whole microscope greatly reduces focus drifts due to room temperature fluctuations, but numerous drawbacks include expensive and customized construction, obstruction of access to microscope, and high consumption of energy and gases. Also, exposure to humidity and repeated temperature changes may damage microscopes.

Stagetop incubators surround only a small volume intended to house one or more Petri dishes, slides or other culture platform. These provide local temperature regulation and enable limited gas environment control. They are convenient, but do not provide the same level of control as a microscope enclosure, as the stagetop incubator must mimic the mechanics of an enclosure, but in a smaller size and adapt to the microscope. For example, uniform temperature control in a stagetop incubator is limited by the heat sink of the stage itself, and cutouts to provide for the light path for optical clarity further reduce uniformity. In addition, the complexity of the design of stagetop incubators make them expensive.

Perfusion chambers generally consist of an assembly that encloses a flowing liquid volume, with heating elements either directly through the walls of the chamber or immediately upstream of the inlet flow path. The design of the control elements need to be carefully considered, as issues such as heat/mass transfer may make proper maintenance of a steady state condition difficult. At present, flow chambers are infrequently used in live cell imaging due to the myriad difficulties of adapting them for typical uses.

The present invention, by contrast, integrates temperature, flow, and gas control directly to a microfluidic culture plate via the use of a manifold that seals to the microfluidic plate. While manifolds similar in some aspects are discussed in some of the above referenced applications to control perfusion on microfluidic plates, the previous designs did not incorporate all of the features described herein as such incorporation was difficult due to the compact nature of the manifold and culture plate. The present manifold design includes novel temperature or gas "microincubator" compartments created by operation of the manifold. These compartments have been demonstrated to provide novel and critical advantages for the proper integration for live cell imaging needs.

The present invention enables direct cell culture on a microscope stage without the use of external environment chambers such as enclosures or stage-top heaters. The "microincubator" concept according to specific embodiments of the present invention provides precise control, long-term cell culture, and ease of dynamic changes of conditions that has not been available in this context in other designs.

While many of the examples discussed in detail herein are designed to be used in conjunction with a standard or custom well plate, according to specific embodiments the microfluidic structures and culture units and systems and methods of various configurations as described herein can also be deployed independently of any well-plate, such as in various integrated lab-on-a-chip systems that are not configured to be used in conjunction with well plates or various other microfluidic devices or systems.

For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. Unless specifically stated otherwise herein, any combination of elements described herein should be understood to include every sub-combination of any subset of those elements and also any sub-combination of any subset of those elements combined with any other element described herein or as would be understood to a practitioner of skill in the art.

In some of the drawings and detailed descriptions below, the present invention is described in terms of the important independent embodiments of multi-component devices or systems. This should not be taken to limit various novel aspects of the invention, which, using the teachings provided herein, can be applied to a number of other situations. In some of the drawings and descriptions below, the present invention is described in terms of a number of specific example embodiments including specific parameters related to dimensions of structures, pressures or volumes of liquids, temperatures, electrical values, durations of time, and the like. Except where so provided in the attached claims, these parameters are provided as examples and do not limit the invention, which encompasses other devices or systems with different dimensions. For purposes of providing a more illuminating description, particular known fabrication steps, cell handling steps, reagents, chemical or mechanical process, and other known components that may be included to make a system or manufacture a device according to specific embodiments of the invention are given as examples. It will be understood to those of skill in the art that except were specifically noted herein otherwise, various known substitutions can be made in the processes described herein.

All references, publications, patents, and patent applications cited in this submission are hereby incorporated by reference in their entirety for all purposes.

BRIEF DESCRIPTION OF THE DRAWINGS

FIG. 7 is a schematic side view of the pneumatic portions of a manifold sealed to a culture plate and showing the gas in lines connecting to an environment control volume according to specific embodiments of the invention.

FIG. 9 illustrates a manifold with additional gas line and a heated objective lens according to an earlier manifold design.

FIG. 10A-C shows a top view, side view, and plan view of a schematic of an example pneumatic manifold according to earlier designs. In this example, the eight tubing lines to the right are for compressed air, and each is configured to provide pressure to a column of cell inlet wells in a microfluidic array. The left-most line in the figure is for vacuum and connects to an outer vacuum ring around the manifold. This basic manifold design is modified using the teachings herein to produce the heated manifold.

FIG. 13 shows NIH-3T3 mouse fibroblasts cultured using the microincubator system according to specific embodiments of the invention at t=0 (left) and after 15 hours (right) showing cell growth and viability. When no temperature or $CO_2$ was controlled, the cells rapidly died within 2 hours.

FIG. 19 (Table 1) illustrates an example of diseases, conditions, or states that can be evaluated or for which drugs or other therapies can be tested according to specific embodiments of the present invention.

DETAILED DESCRIPTION OF SPECIFIC EMBODIMENTS

1. Overview

Definitions

Figure 1:
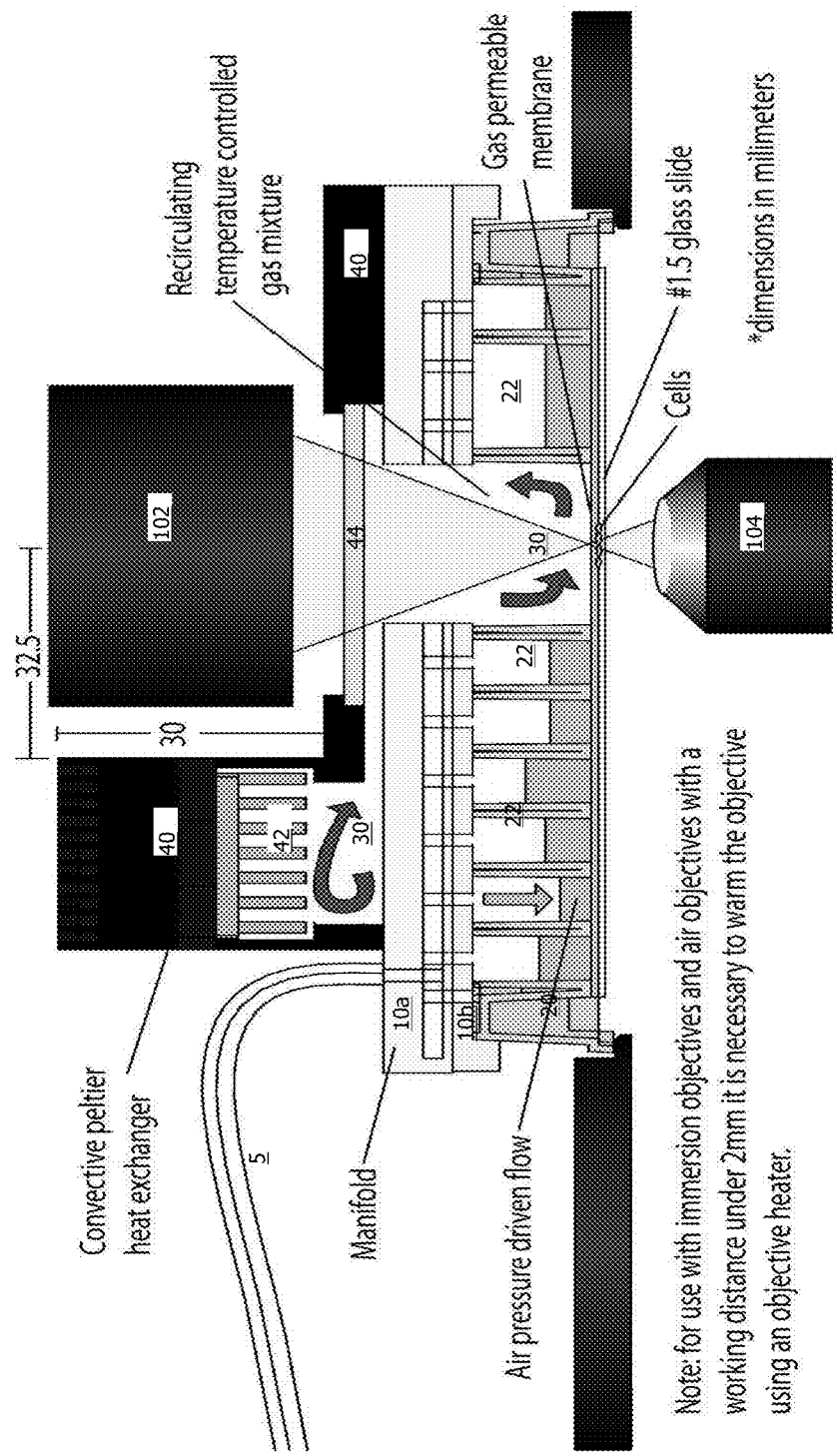
FIG. 1 shows a side view of an example micro-incubator manifold according to specific embodiments of the invention shown in place in a micro-incubator system with a well plate and microscope viewer.

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microchannel" or "channel" or "flow channel" generally refers to a micron-scale channel used for fluidically connecting various components of systems and devices according to specific embodiments of the invention. A microchannel typically has a rectangular, e.g., square, or rounded cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably. "Flow channel" generally denotes channels designed for passage of media, reagents, or other fluids or gels and in some embodiments cells. "Culture channel" or "cell culture channel" generally denotes a portion of a cell culture structure that cells are designed to flow through and also remain during cell culture (though the cells may be localized into a particular culture area of the culture channel in some embodiments). "Air channel" generally denotes a roughly micron-scale channel used for allowing gases, such as air, oxygen enriched mixtures, etc., to pass in proximity to flow channels or culture areas. "Perfusion channel" is sometimes used to indicate a flow channel and any perfusion passages or structures that allow media to perfuse to the culture area.

A "perfusion barrier" refers to a combination of solid structures and perfusion passages that generally separate a flow channel from a cell culture area or chamber. The perfusion passages are generally smaller than the microchannel height and/or width (for example, on the order of 5-50% or on the order of about 10%) and are designed to keep cells, other culture items, and in some embodiments gels, from migrating into the flow channels, while allowing some fluidic flow that is generally of a much higher fluidic resistance than the fluid flow in the flow channels. In one example embodiment, the perfusion barrier has a perfusion passage that is 4 microns high and that otherwise runs most of the length of the microchannel. In other embodiments, a perfusion barrier has many perfusion passages that are about as high as the microfluidic channel, but about 4 microns wide.

A "microfluidics device" refers to a device having various station or wells connected by micron-scale microchannels in which fluids will exhibit microfluidic behavior in their flow through the channels.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

Microfluidic systems provide a powerful tool to conduct biological experiments. Recently, elastomer-based microfluidics has especially gained popularity because of its optical transparency, gas permeability and simple fabrication methods. The present invention involves integrated microfluidics used for various culture and assay applications and systems for providing heating control and automating various handling of culture plates. Advantages of specific embodiments include use of a standard-sized microtiter plate format, tubing free plates, and easy and effective mating of plates with a manifold to provide gas recirculation and heating control.

According to further embodiments of the invention, as has been previously described, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates. In the present invention, heating and gas circulation elements are incorporated into the manifold to provide a micro-incubator system.

In further embodiments, a gravity driven flow culture configuration utilizes the medium level difference between the inlet and outlet well as well as engineering the fluidic resistances to achieve the desirable flow rate in nL/min regime can be used to "passively" flow culture medium for long periods of time (e.g., up to 4 days) without the use of bulky external pumps or tubes in an environment such as an incubator to control temperature and then the heat controlled manifold, as provided herein, can be used for control of the cell culture during observation.

In some embodiments, a custom pneumatic flow controller can be attached to the gas and electric connectors in the manifold and thereby used to load the cells into the culture regions, to switch between different exposure solutions, and to control the temperature of the culture region. A digital software interface can be used to allow a user to program specific inputs (pulses, ramps, etc.) over time to expose the cells to complex functions during time-lapse imaging while maintaining or varying temperature and gas exposure as desired.

2. Microfluidic Culture System and Array

The applications referenced above discussed a variety of different cell culture configurations and fabrication techniques. Portions of the operation of the cell culture areas and materials are useful as background to the present discussion. In some examples therein, one or more micro culture areas are connected to a medium or reagent channel via a grid of fluidic passages (or diffusion inlets or conduits), wherein the grid comprises a plurality of intersecting high fluidic resistance perfusion passages. In one discussed example, passages in the grid are about 1 to 4 $\mu$m in height, 25 to 50 $\mu$m in length and 5 to 10 $\mu$m in width, the grid allowing for more even diffusion between medium or reagent channels and the culture area and allowing for easier manufacturing and more even diffusion. The earlier application further discussed that the high fluidic resistance ratio between the microchamber and the perfusion/diffusion passages or grid (e.g., ratios in the range of about 10:1, 20:1 to 30:1) offers many advantages for cell culture such as: (1) size exclusion of cells; (2) localization of cells inside a microchamber; (3) promoting a uniform fluidic environment for cell growth; (4) ability to configure arrays of microchambers or culture areas; (4) ease of fabrication, and (5) manipulation of reagents without an extensive valve network. Examples were illustrated wherein a grid-like perfusion barrier can be much shorter than the culture area or can be near to or at the same height, according to specific embodi-

3. Pneumatic Manifold with Heat Control

Figure 11:
FIG. 11 illustrates an example microfluidic perfusion system (ONIX™), microincubator controller and manifold (MIC) according to specific embodiments of the invention.

As discussed above, one difficulty in a number of culture systems is how to control the heating and temperature of the culture area while allowing for observation of the cellular processes. Previous solutions have relied on heating sources applied to the well-plate, for example, from the microscope viewer. (E.g., see FIG. 11), or containing the entire system in a controlled environment.

Figure 2:
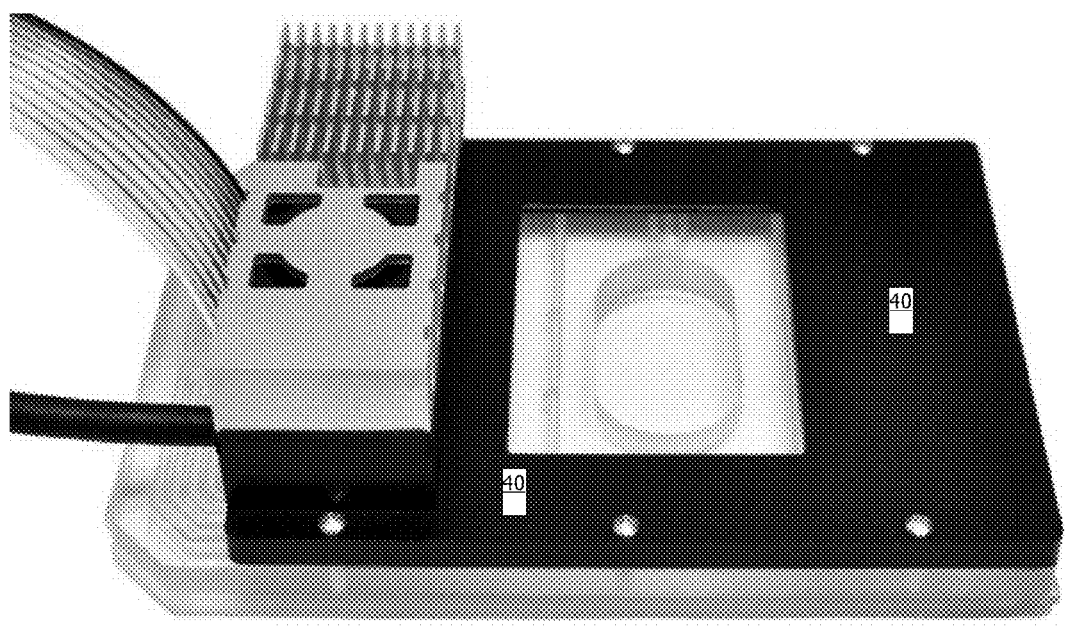
FIG. 2 illustrates one example of a top plane view of a manifold with a heat controller according to specific embodiments of the invention.
Figure 3:
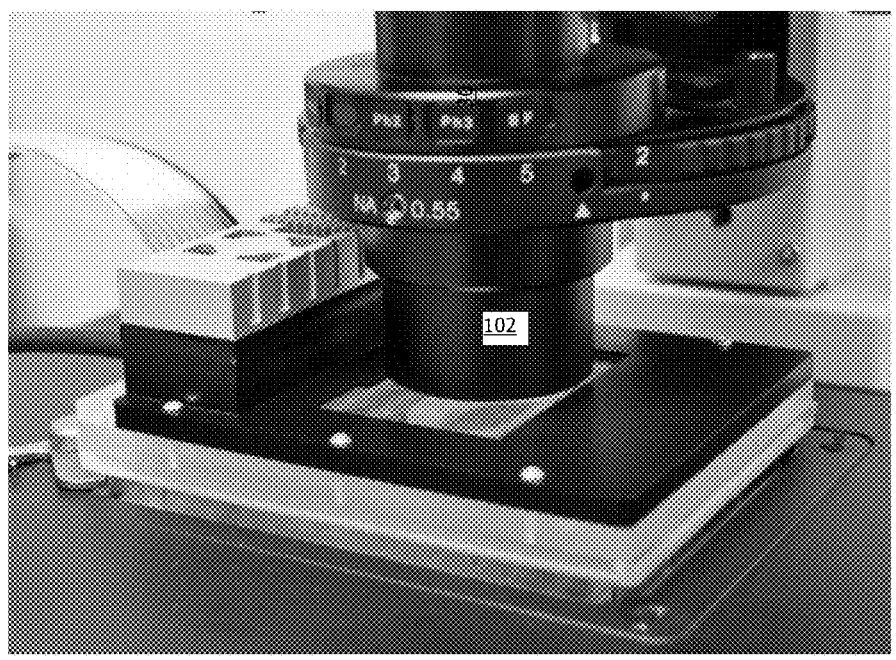
FIG. 3 illustrates one example of a topside view of a manifold with a heat controller sealed to a well-plate and mounted in a microscope viewer according to specific embodiments of the invention.
Figure 4:
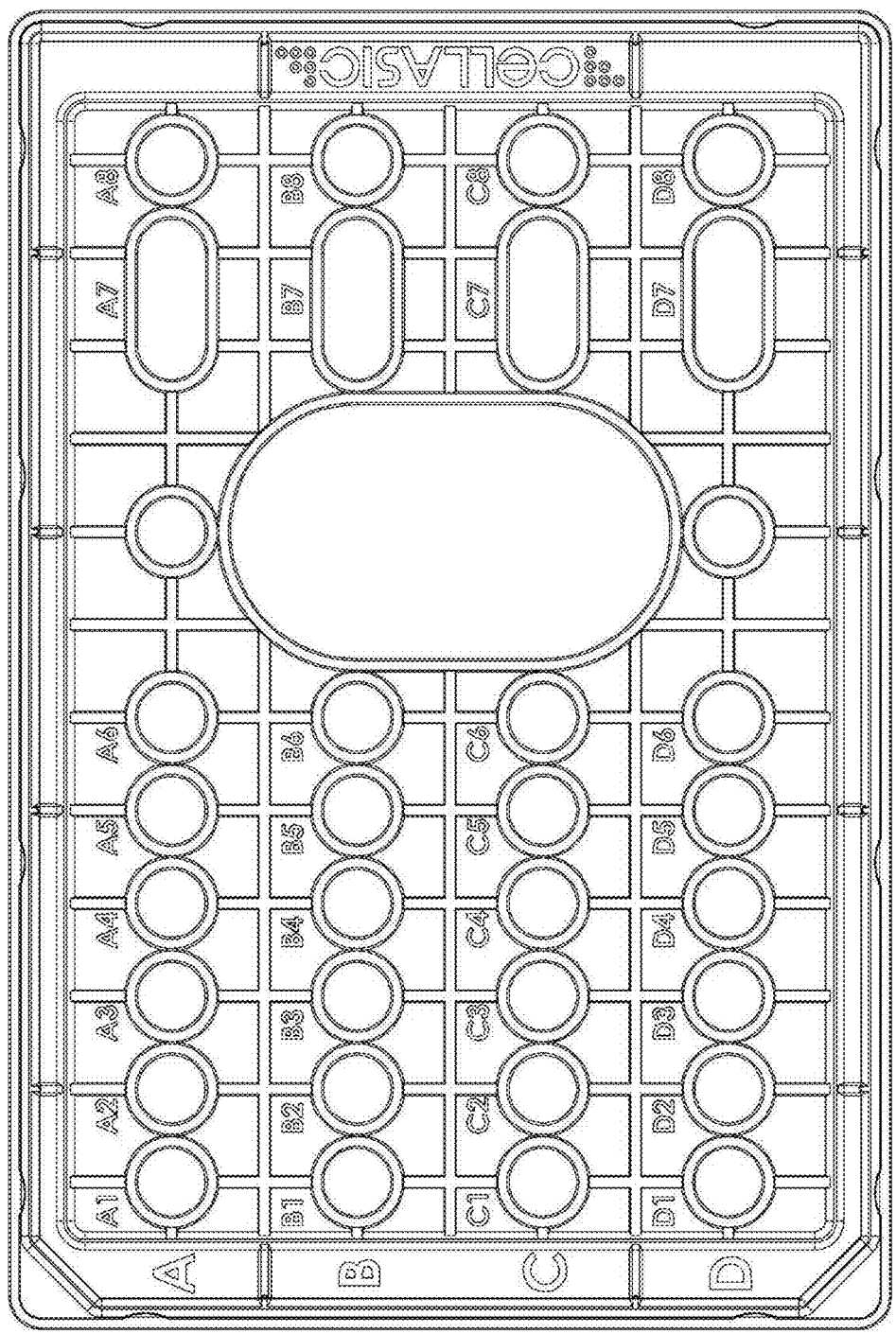
FIG. 4 illustrates one example of a culture plate with four culture units placed onto a 96-well standard SBS plate. This example shows four culture units (corresponding to rows labeled A-D) with six inlet wells (labeled A1-D6), four microfluidic culture areas placed under the large viewing oval, and two outlet wells (7-8). This is an example only and placement and designation of the various wells and components will vary with different implementations.
Figure 5A:
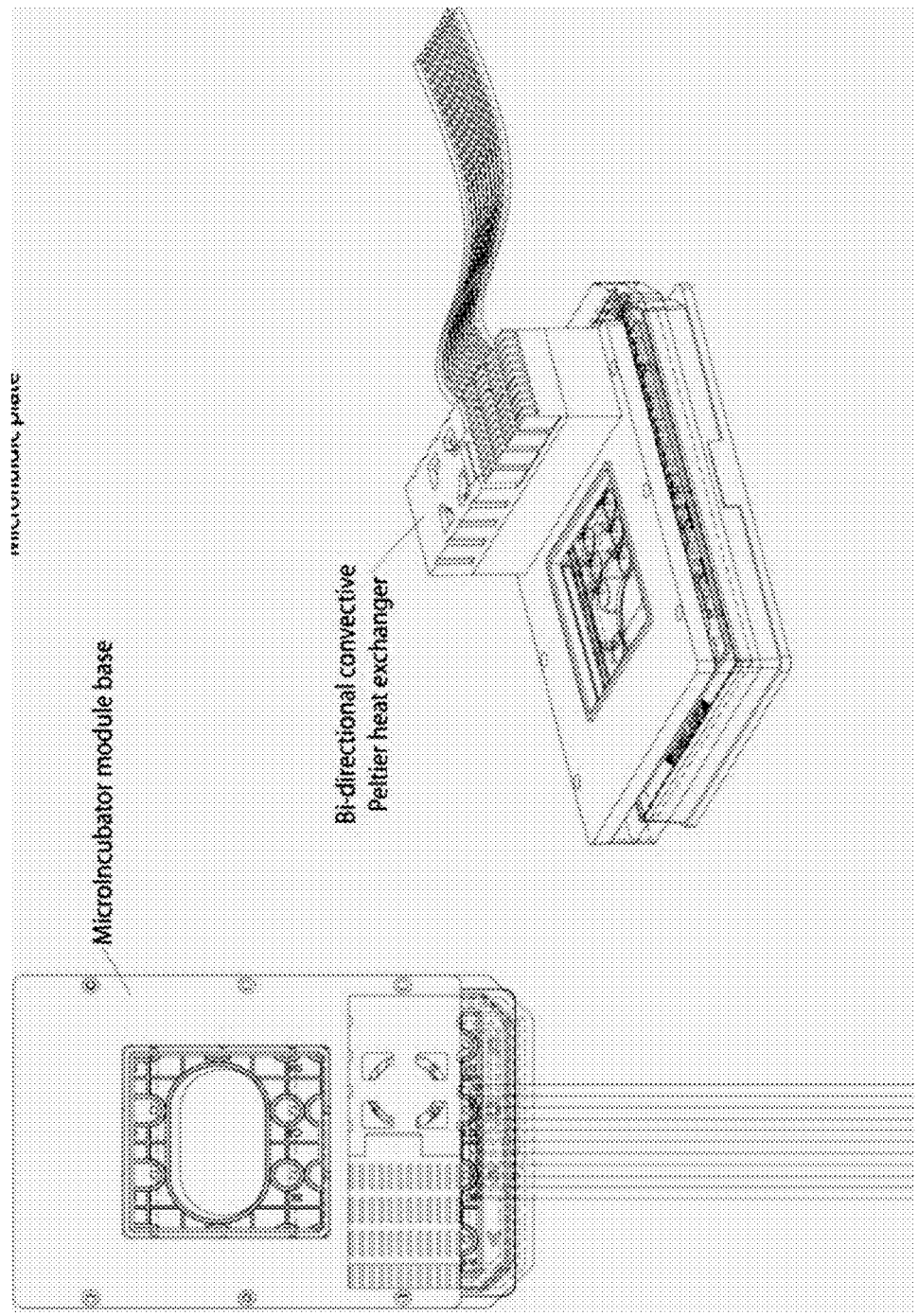
FIG. 5A-D are schematic drawings of an example implementation of a manifold with a heat controller from various views according to specific embodiments of the invention.
Figure 5B:
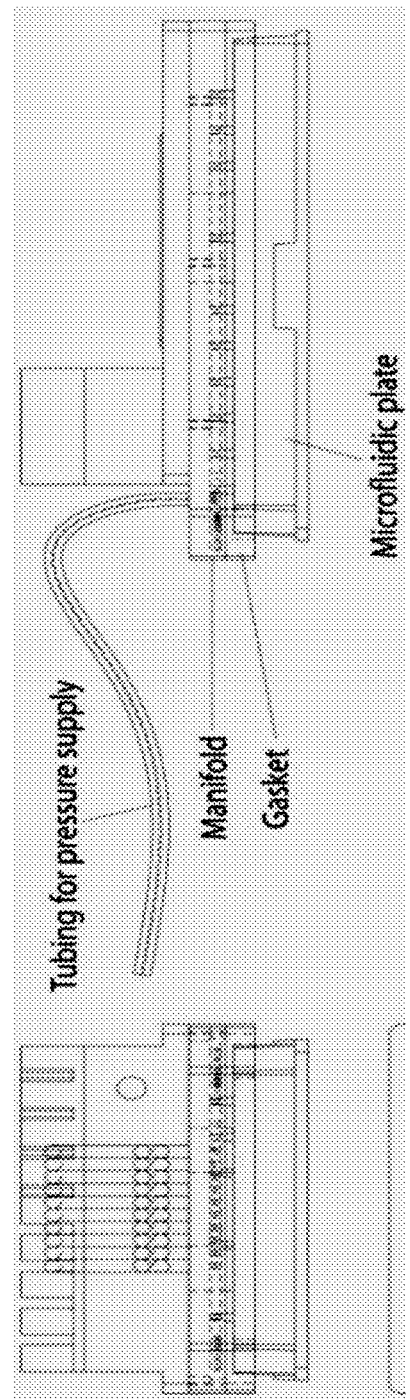
Figure 5C:
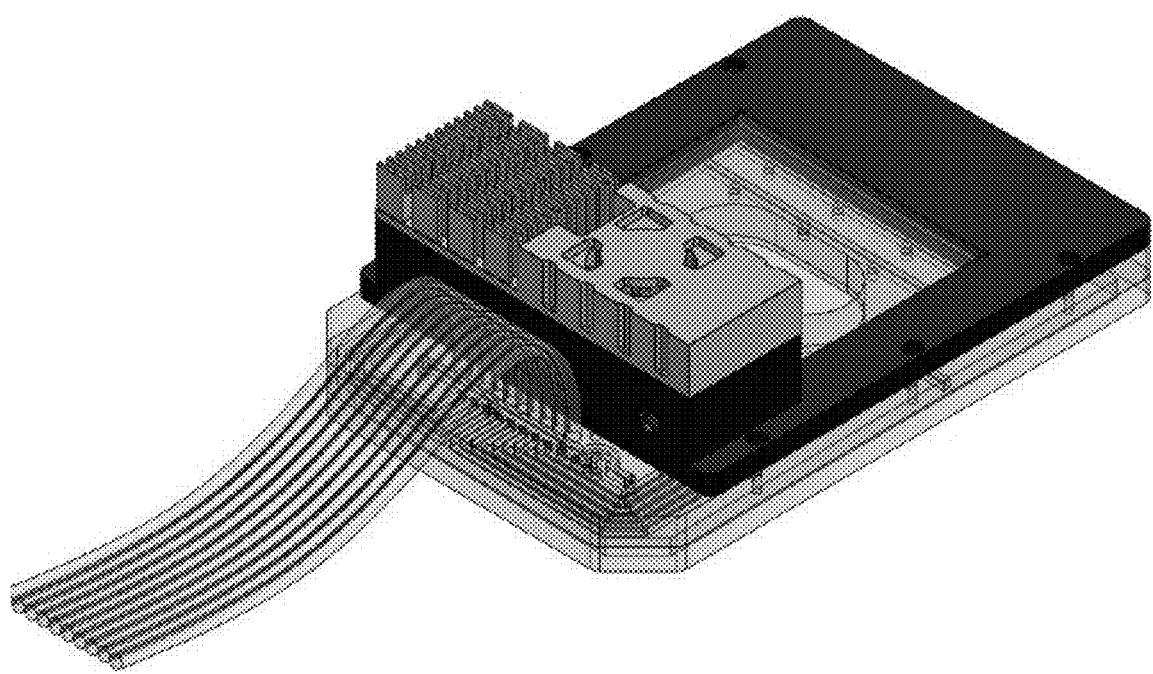
Figure 5D:
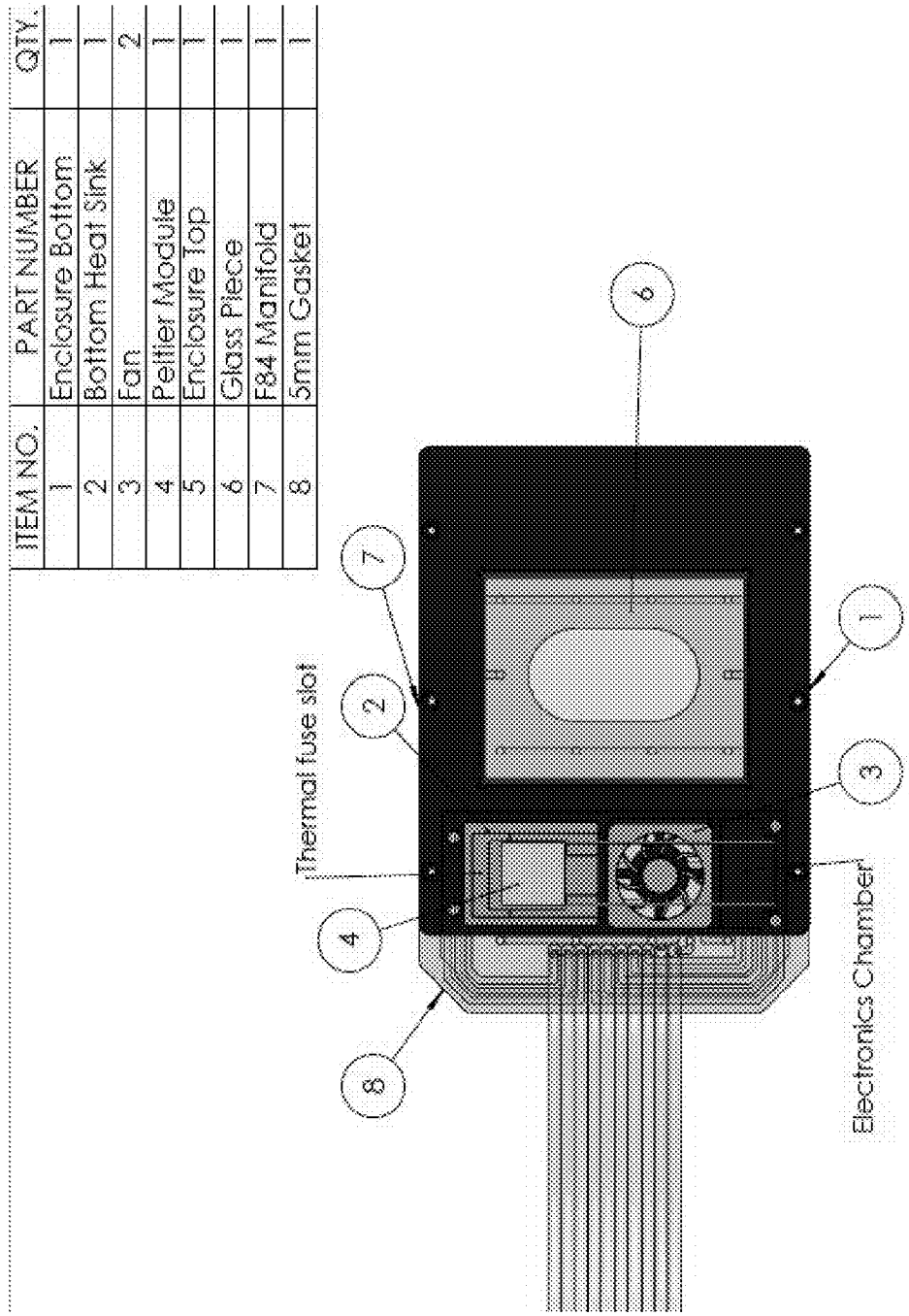

The present invention provides an improved culture system by placing all or nearly all heat and gas controls in or attached to a typically removable manifold that in preferred embodiments is configured to be operational will not interfering with observational equipment. The invention will be more easily understood with reference to the specific examples illustrated, though these examples are intended to be illustrative and not limiting. FIG. 1 shows a side view of an example micro-incubator manifold according to specific embodiments of the invention shown in place in a micro-incubator system with a well plate and microscope viewer. FIG. 2 illustrates one example of a top plane view of a manifold with a heat controller according to specific embodiments of the invention. FIG. 3 illustrates one example of a topside view of a manifold with a heat controller sealed to a well-plate and mounted in a microscope viewer according to specific embodiments of the invention. FIG. 4 illustrates one example of a culture plate with four culture units placed onto a 96-well standard SBS plate. This example shows four culture units (corresponding to rows labeled A-D) with six inlet wells (labeled A1-D6), four microfluidic culture areas placed under the large viewing oval, and two outlet wells (7-8).

Thus, according to specific embodiments, a MicroIncubator Manifold can interface to a variety of microfluidic plates and provides one or more of cell-loading, perfusion, temperature and gas environment control. A convective heat exchanger adds or removes heat to the gas mixture using a Peltier thermoelectric device. The cells are kept warm through conducted heat from the warm gas mixture and the desired gas concentration diffuses in the media surrounding the cells through a gas permeable membrane on the microfluidic plate.

As can be seen from FIG. 1, when the manifold according to specific embodiments is in place over a culture plate, a sealed gas chamber is formed from the heat exchanger, under the manifold and into the area above the culture microfluidics. Gas introduced into the area above the microfluidics is circulated by a fan or other gas circulatory means in the heat exchanger, thereby providing control of both the gas environment and the temperature above the culture area using the manifold.

This design, according to specific embodiments of the invention, solves the problem of providing effective heating in a small space to deliver the controlled temperature to the cells themselves while also controlling the gas composition. According to specific embodiments of the invention, the microincubator manifold includes both a gas input and a recirculating fan to control the gas composition.

In the example implementation shown in FIG. 1, controlled and pressurized gases enter the manifold through the gas lines 5. The pneumatic portion of the manifold is shown for convenience in this example in two pieces, top piece 10a and bottom piece 10b, which comprises a gasket for tightly fitting to plate 20, the plate containing a number of wells 22. The pneumatic operation of the manifold and fitting to the well plate is as described in herein referenced patent applications. The manifold also includes heat exchange module 40, with internal heat exchange fins 42 and a transparent cover plate (e.g., glass or acrylic) 44. When the manifold is placed over plate 10, the open region above the culture areas is connected with the heating element to create a gas circulation region 30. To show the device in context, microscope and lighting elements 102 and 104 are illustrated as they would generally be used in operation. The well plate can be any standard or custom well plate as described herein. It will be understood from the teachings provided herein that different configurations of manifold 40 are constructed to accommodate different well plate designs.

Recirculating on the Manifold.

In this example design, the gas and heating controls and elements are entirely contained in the manifold and the manifold can mate with any number of differently configured micro-well plates, including microwell plates that have no specific modifications to allow them to receive a heat source.

According to specific embodiments, two fans are used in the heat exchange element one to circulate the sealed gas in the gas area and one to interact with the heat exchanger.

FIG. 5A-D are schematic drawings of an example implementation of a manifold with a heat controller from various views according to specific embodiments of the invention. The pneumatic portions of the manifold operate similarly to previously disclosed designs. The heat exchange module is described in more detail below.

Manifold Heat Exchange Module

A heat exchange module in one example embodiment controls the temperature within the chamber by the cycling of air at desired temperature. In specific embodiments, temperature control is provided by a thermoelectric Peltier module, which are well known devices that convert an electric current into a temperature gradient and can also be used as a temperature controller that either heats or cools. While other heating sources can be used in a manifold of the invention, a Peltier module is a presently preferred mechanism as it can be fully incorporated into the heat exchange module and the manifold.

A heat exchange module in an example implementation has three main outer pieces: (1) a metal top enclosure, (2) a plastic bottom enclosure and (3) a manifold with an oval cutout that allows air to flow into the cell culturing chamber of the plate and cycle back out.

Plastic Bottom Enclosure

Figure 6A:
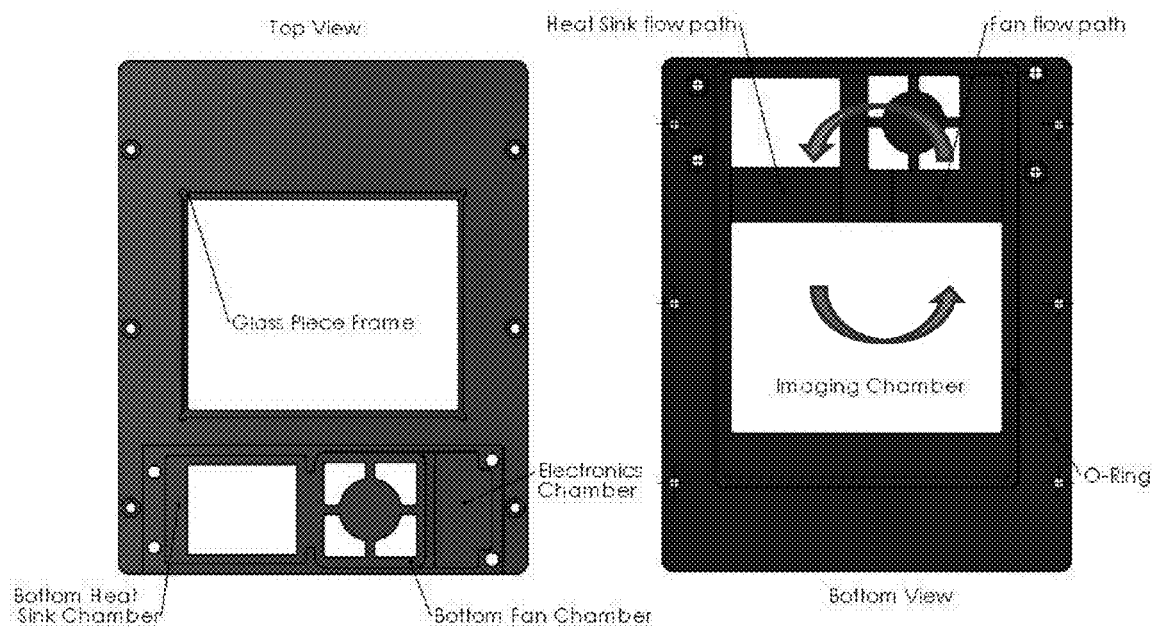
FIG. 6(A) illustrates the bottom portion of a heat exchange module according to specific embodiments of the invention. The bottom portion attaches to the pneumatic portion of the manifold. (B) illustrates the top portion of a heat exchange module according to specific embodiments of the invention.

FIG. 6(A) illustrates the bottom portion of a heat exchange module according to specific embodiments of the invention. The bottom portion attaches to the pneumatic portion of the manifold. (B) illustrates the top portion of a heat exchange module according to specific embodiments of the invention. In a specific embodiment, the plastic enclosure of the bottom portion is attached to the top of the manifold (or example by screws or glue or other means). The bottom of this enclosure has a cut out of two 2 mm deep flow paths. These paths merge into one over the imaging chamber. When they merge, the depth of the path rises to 3 mm. Around the outskirt of the flow path is an o-ring that prevents the exchange of air between the flow path and the environment. The size of the flow paths must be wide enough to allow a desirable amount flow to circulate into the cell culture chamber. This decreases the difference in temperature in the plate cell culturing region and the Heat Exchange Module (at the location of the temperature probe).

A vertical extrusion sits above the paths. It contains 3 chambers. Above one flow path is a heat sink and above the other sits a fan. The third chamber connects to another chamber in the metal top enclosure to make room for a PCB board that connects the wires of the Peltier module, a small temperature probe, a relay, connections to the microincubator controller and 2 thermal cutoffs (one for each heat sink). The temperature probe is routed from the electronics chamber through a screw hole on the fan and into the top of its flow path to measure the temperature of air cycling through.

The plastic enclosure also has a cut out from the top that forms a frame for a piece of 2 mm glass. This piece of glass sits right above the cell culturing chamber in order to create optimal condition for microscope imaging without disrupting heating.

Metal Top Enclosure

Figure 6B:
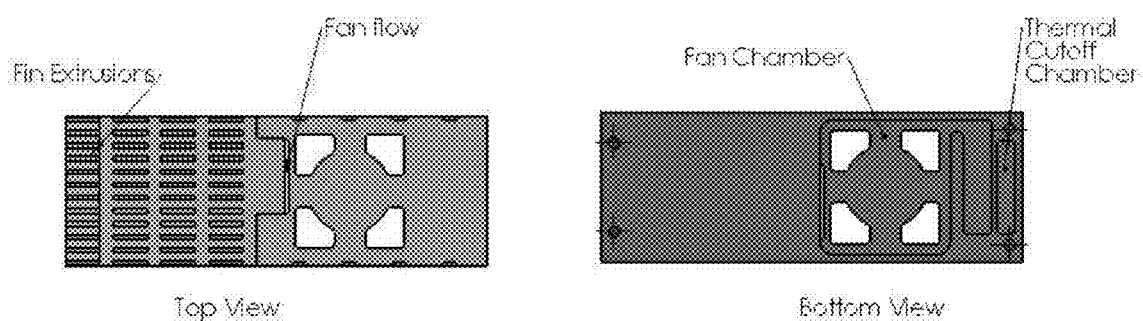

The metal top enclosure (FIG. 6B) has fin extrusion features that allow it to act as a heat sink for the other side of the Peltier module. In addition, it optionally contains a chamber for a second fan to speed up the cooling process as well as room for a thermal cutoff that connects to the electronics chamber of the plastic bottom enclosure.

After the fan is placed inside the enclosure and the thermal cutoff attached to the smaller chamber, thermal grease is applied to the top of the Peltier module in order to attach it to the metal top enclosure. In a specific example, the bottom of the plastic enclosure is securely fastened to the top enclosure, for example using screws or glue.

When temperature in the cell culturing region has to be raised, the Peltier module heats up the bottom heat sink by cooling the top heat sink. The bottom fan blows hot air across the bottom heat sink into the flow path beneath it. The heated air enters the cell culturing chamber as cooler air is circulated back to the fan. When temperature in the culturing region has to be lowered, the Peltier module cools the bottom heat sink by raising temperature on the top (up to ambient temperature).

FIG. 7 is a schematic side view of the pneumatic portions of a manifold sealed to a culture plate and showing the gas in lines connecting to an environment control volume according to specific embodiments of the invention.

Figure 8:
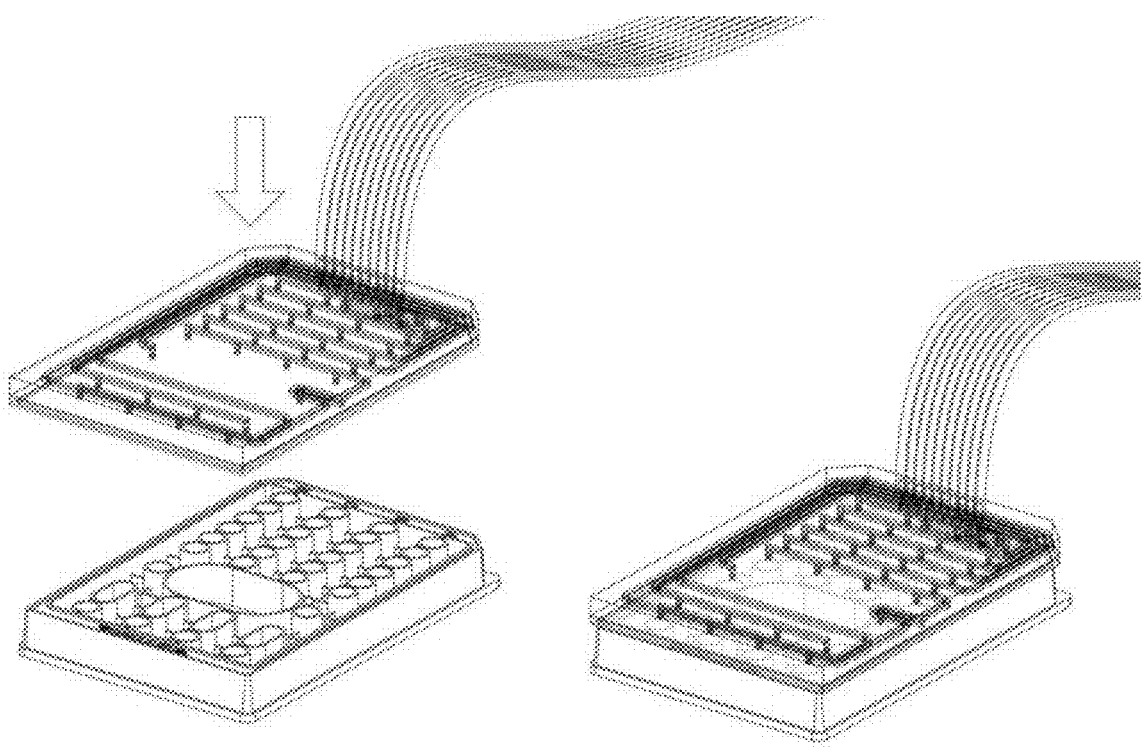
FIG. 8 is a schematic showing how a manifold interfaces to a microfluidic plate according to specific embodiments wherein a positive seal is created by applying a vacuum to the cavity surrounding all the wells. The heating unit is not shown in this figure.

FIG. 8 is a schematic showing how a manifold interfaces to a microfluidic plate according to specific embodiments wherein a positive seal is created by applying a vacuum to the cavity surrounding all the wells. The heating unit is not shown in this figure.

4. Earlier Pneumatic Manifold

While gravity or passive loading is effective for some microfluidic cell culture devices and desirable in some embodiments, a proprietary pneumatic manifold was previously described in the above referenced applications. This may be mated to the plate and pneumatic pressure is applied to the cell inlet area for cell loading and for culturing during invasion assays. FIG. 10A-C shows a top view, side view, and plan view of a schematic of an example pneumatic manifold according to earlier designs. In this example, the eight tubing lines to the right are for compressed air, and each is configured to provide pressure to a column of cell inlet wells in a microfluidic array. The left-most line in the figure is for vacuum and connects to an outer vacuum ring around the manifold. The manifold is placed on top of a standard well plate. A rubber gasket lies between the plate and manifold, with holes matching the manifold (not shown). The vacuum line creates a vacuum in the cavities between the wells, holding the plate and manifold together. Pressure is applied to the wells to drive liquid into the microfluidic channels (not shown). A typical pressure of 1 psi is used; therefore the vacuum strength is sufficient to maintain an air-tight seal. In one example there are 9 tubing lines to the pressure controller: 8 lines are for compressed air and 1 line is for vacuum (left-most). In specific example embodiments, each column is connected to a single pressure line. Columns above the cell imaging regions are skipped.

Pressurized cell loading has been found to be particularly effective in preparing cultures of aggregating cells (e.g., solid tumor, liver, muscle, etc.). Pressurized cell loading also allows structures with elongated culture regions to be effectively loaded. Use of a pressurized manifold for cell loading and passive flow for perfusion operations allows the invention to utilize a fairly simple two inlet design, without the need for additional inlet wells and/or valves as used in other designs.

While this manifold is effective for cell loading and some perfusion tasks, the manifold did not effectively provide for the recirculation of a gas over the culture area or for any heat control. As illustrated in the figure, heating was provided when necessary from the opposite side of the culture plate, for example form the vicinity of the microscope viewer.

The plate manifold optionally also included an additional "gas line" that is used to bathe the cells in the microfluidic device with a specified gas environment (for example, 5% $CO_2$). Other examples include oxygen and nitrogen control, but any gaseous mixture can be sent to the cells. The gas flows through the manifold into the sealed wells above the cell culture area and holes in the microfluidic device enable the gas to flow into specified microfluidic air channels, as described above. The gas permeable device layer (PDMS) allows the gas to diffuse into the culture medium prior to exposing the cells. By continuously flowing the gas through the microfluidic plate, a stable gas environment is maintained. This provides an optional means for controlling the gas environment to placing the microfluidic plate into an incubator.

Figure 12:
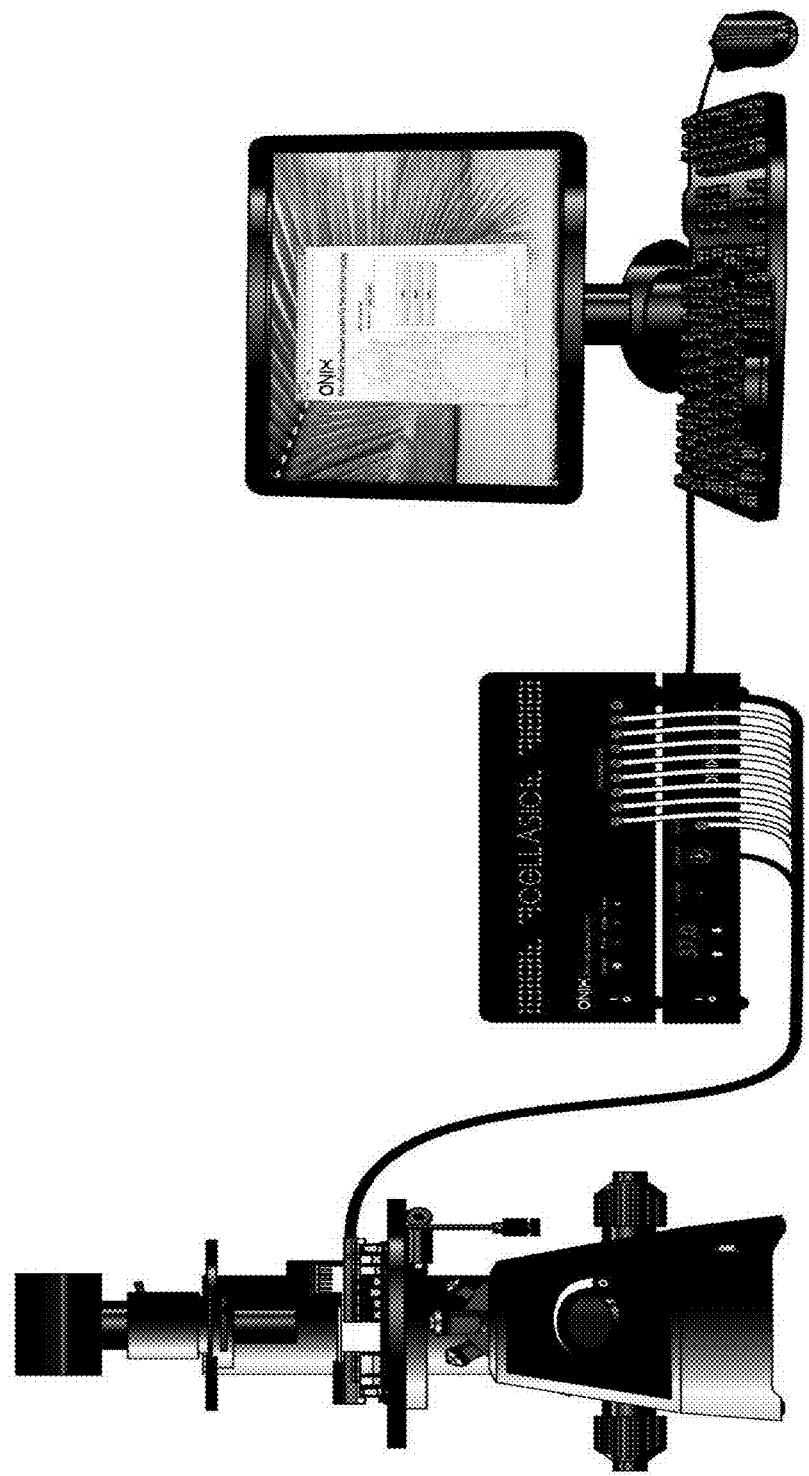
FIG. 12 illustrates an example microfluidic perfusion system (ONIX™), microincubator controller and manifold (MIC) and computer control system according to specific embodiments of the invention.

FIG. 12 illustrates an example microfluidic perfusion system (ONIX™), microincubator controller and manifold (MIC) and computer control system according to specific embodiments of the invention.

Figure 14A:
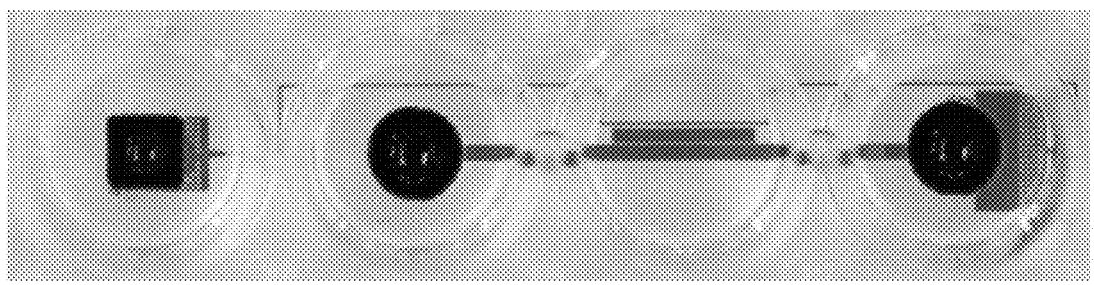
FIGS. 14A-B illustrate one alternative of plate and culture unit design with an example culture unit filled with blue dye with the image taken from top according to specific embodiments of the invention.
Figure 14B:
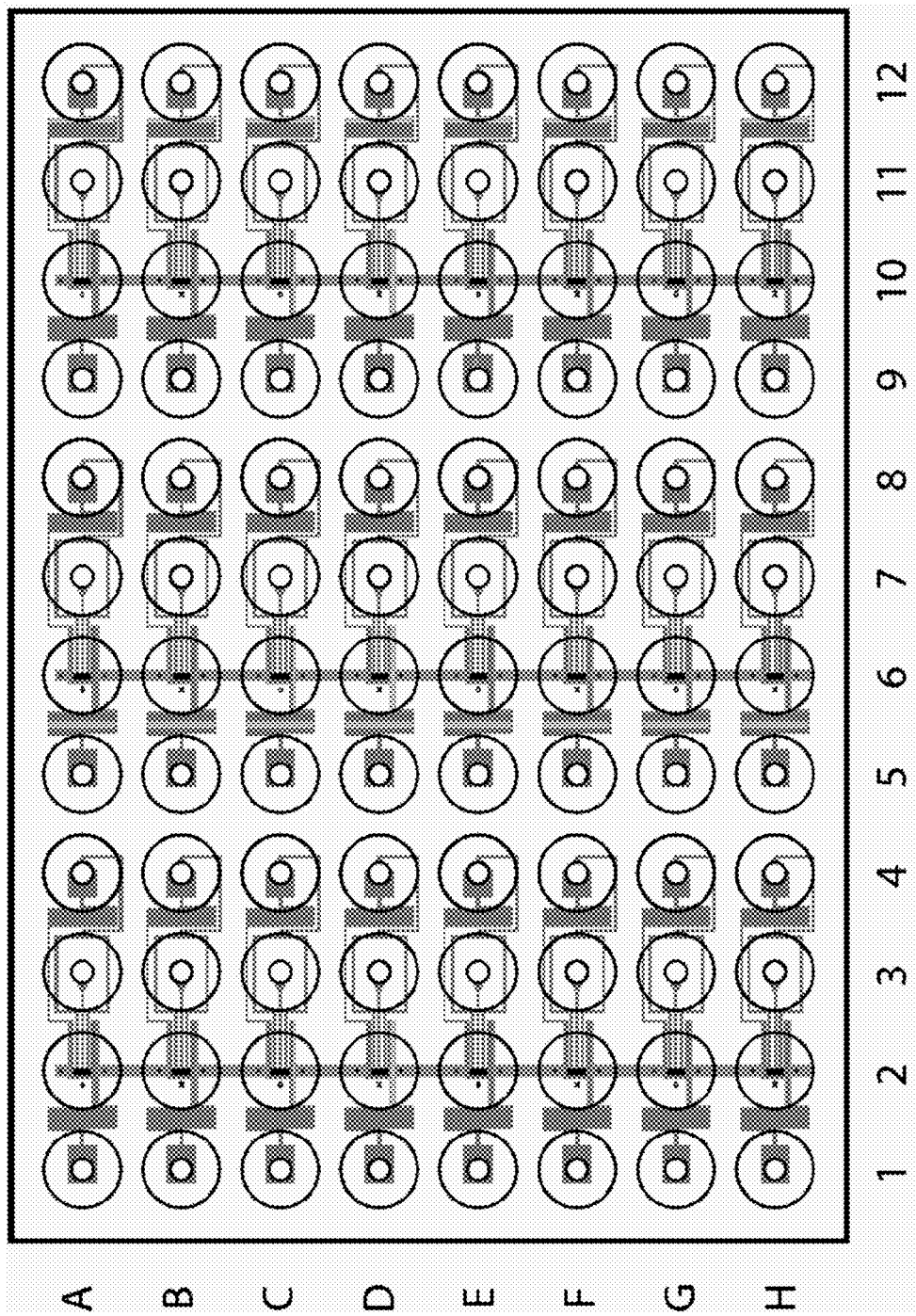
Figure 15:
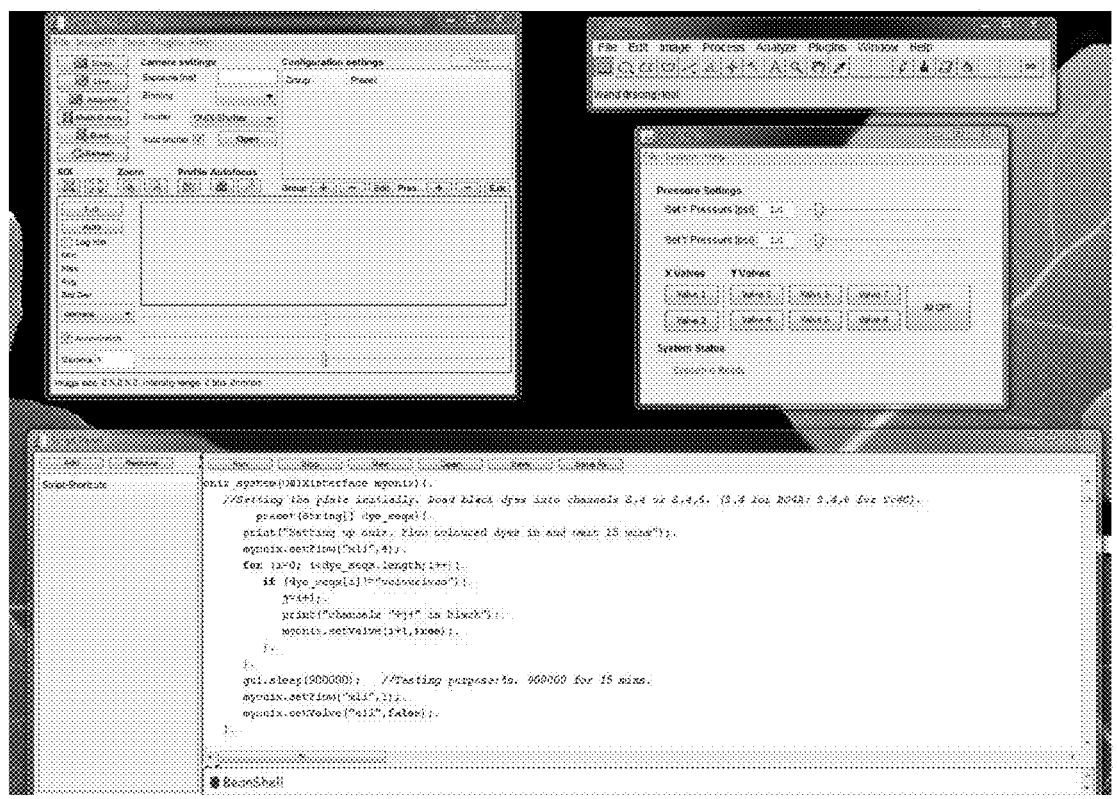
FIG. 15 is a screenshot showing integration of the ONIX microfluidic perfusion system with an open-source microscopy application.
Figure 16:
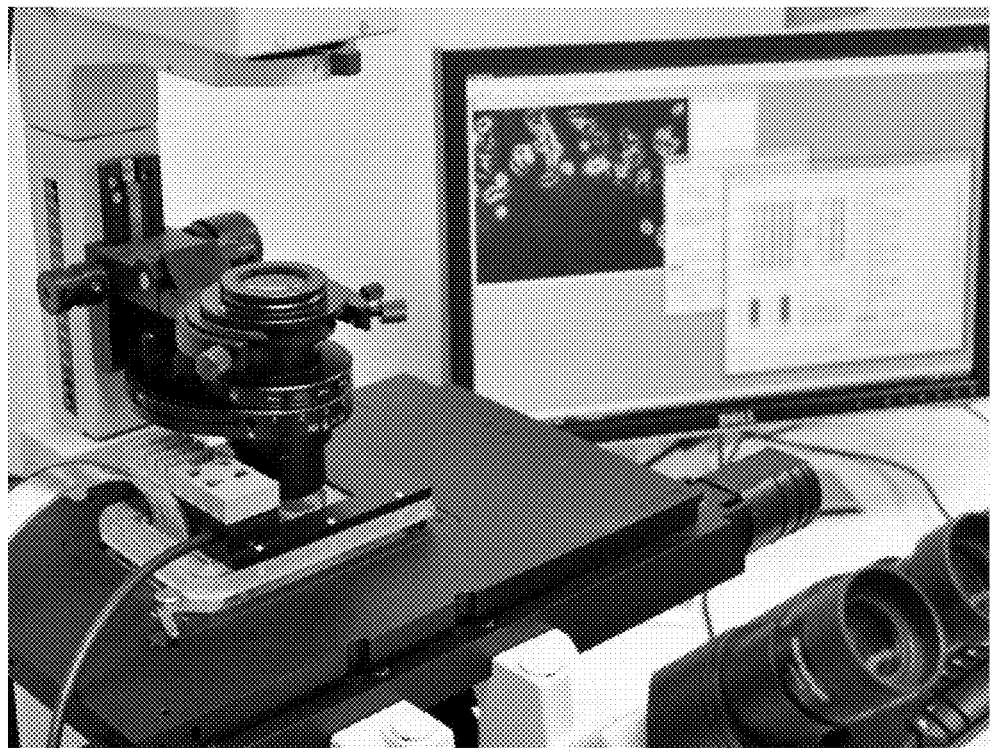
FIG. 16 illustrates a microincubation system integrated with a microscope system for cell analysis. The dimensions of the manifold in specific embodiments allow it to sit on a standard well plate stage, with a transparent optical path that does not interfere with light microscopy. This allows time-lapsed imaging of cells cultured in the micro-incubator.

As just one example, FIG. 14 illustrates one alternative of plate and culture unit design with an example culture unit filled with blue dye with the image taken from top according to specific embodiments of the invention. However, any culture units in any configuration of culture plates can be used with a correctly dimensioned manifold according to specific embodiments of the invention. This includes open top units, invasion units, liver mimetic units, gel units, etc as described in above referenced applications.

Cell Assay and/or Observation

Cell assay can be performed directly on the microfluidic cell culture using standard optically based reagent kits (e.g. fluorescence, absorbance, luminescence, etc.). For example a cell viability assay utilizing conversion of a substrate to a fluorescent molecule by live cells has been demonstrated (CellTiter Blue reagent by Promega Corporation). The reagent is dispensed into the flow inlet reservoir and exposed to the cells via gravity perfusion over a period of time (e.g., 21 hours). For faster introduction of a reagent or other fluid, the new fluid can be added to the flow inlet reservoir followed by aspiration of the cell inlet reservoir.

Data can be collected directly on the cells/liquid in the microfluidic plate, such as placing the plate into a standard fluorescence plate reader (e.g., Biotek Instruments Synergy 2 model). In some reactions, the substrate may diffuse into the outlet medium, and therefore be easily detected in the cell inlet reservoir. For cell imaging assays, the plate can be placed on a scanning microscope or high content system. For example, an automated Olympus IX71 inverted microscope station can be used to capture viability of cultured liver cells with a 20× objective lens.

By repeatedly filling/aspirating the wells, cells can be maintained for long periods of time with minimal effort (e.g. compared to standard "bioreactors" which require extensive sterile preparation of large fluid reservoirs that cannot be easily swapped out during operation).

Example Cell Culture

Cells were cultured using the micro-incubation system to control temperature and gas atmosphere. In one example, human cancer cells (HT-1080, MCF-7, MDA-MB-231) were cultured at 37C and 5% CO2 to monitor cell division over 24 hours. Additional cell types, including yeast, bacteria, primary cells, neurons, etc. have been successfully cultured using the microincubation system. As an example, FIG. 13 shows NIH-3T3 mouse fibroblasts cultured using the microincubator system according to specific embodiments of the invention at t=0 (left) and after 15 hours (right) showing cell growth and viability. When no temperature or CO2 was controlled, the cells rapidly died within 2 hours.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

Figure 17:
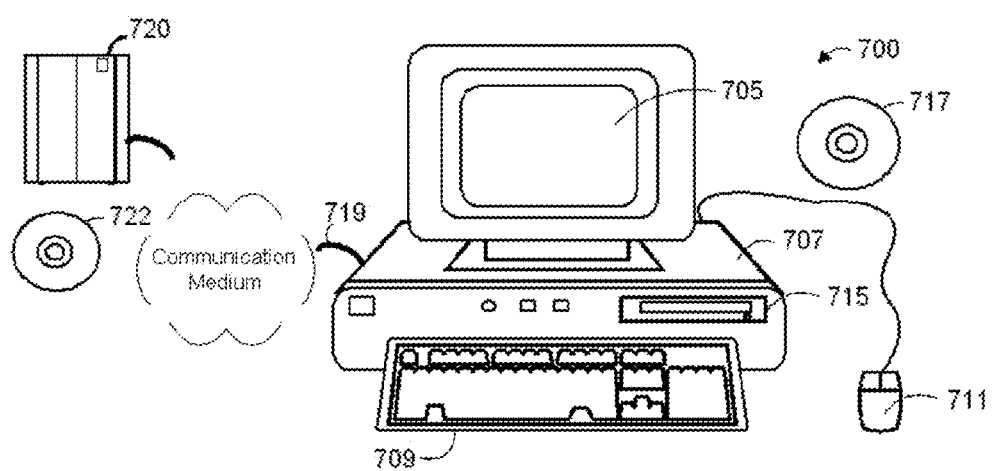
FIG. 17 is a block diagram showing a representative example logic device in which various aspects of the present invention may be embodied.

FIG. 17 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Auto-Sealer Automated System

Figure 18A:
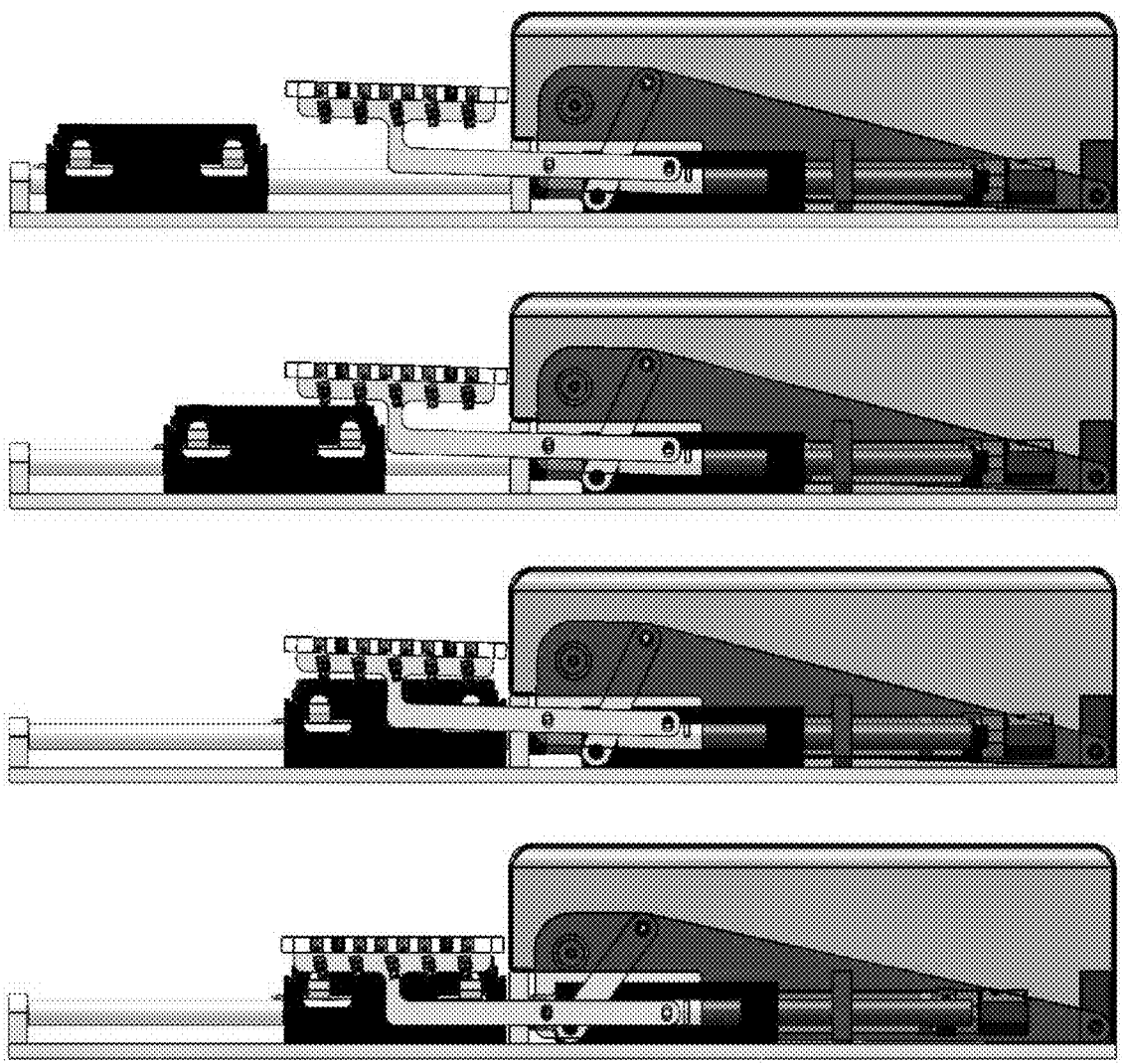
FIG. 18A is a block diagram showing an automated piston driven system according to specific embodiments of the invention.
Figure 18B:
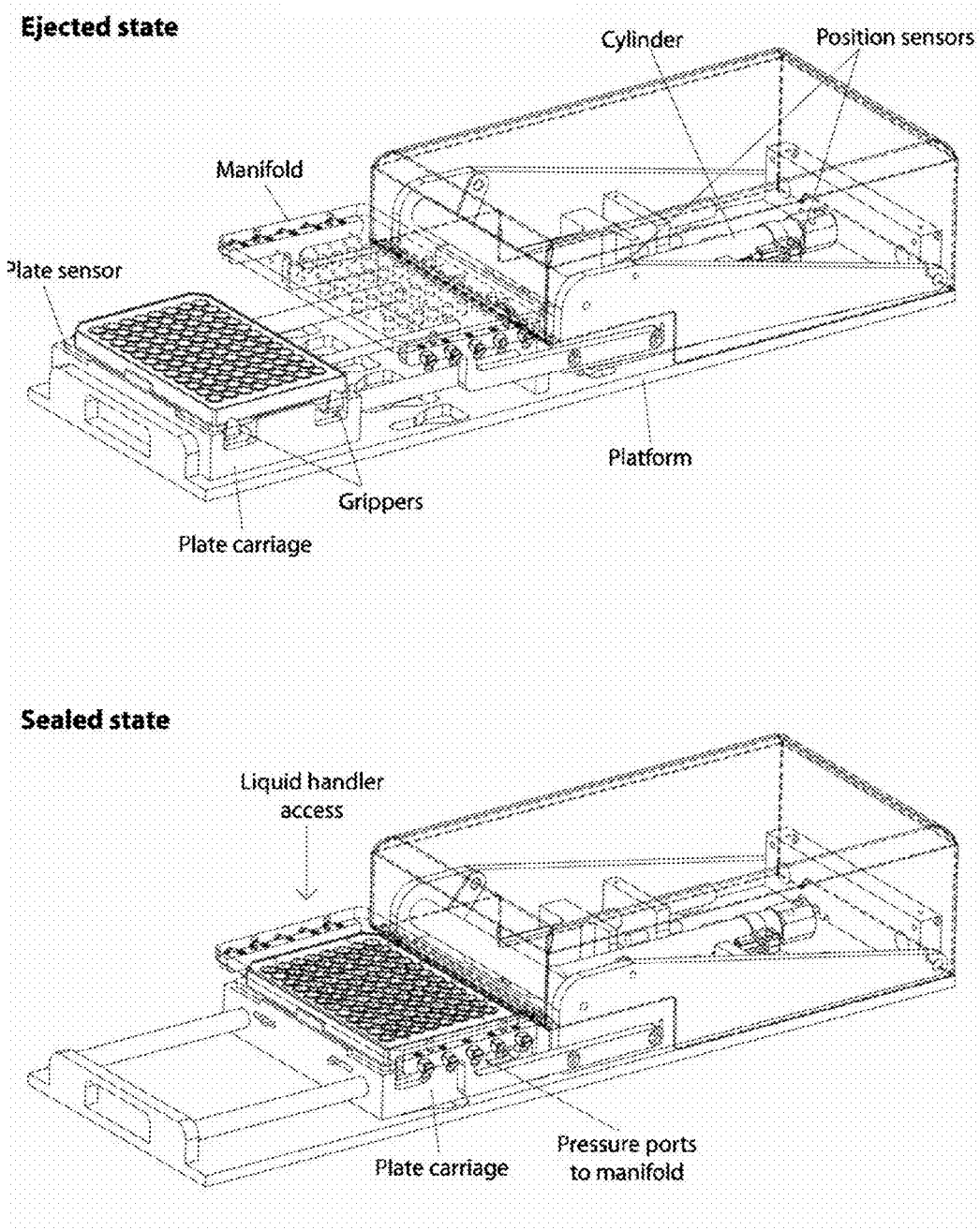
FIG. 18B illustrates perspective views of the automated piston driven system of FIG. 18A in the elected and sealed states.
Figure 20A:
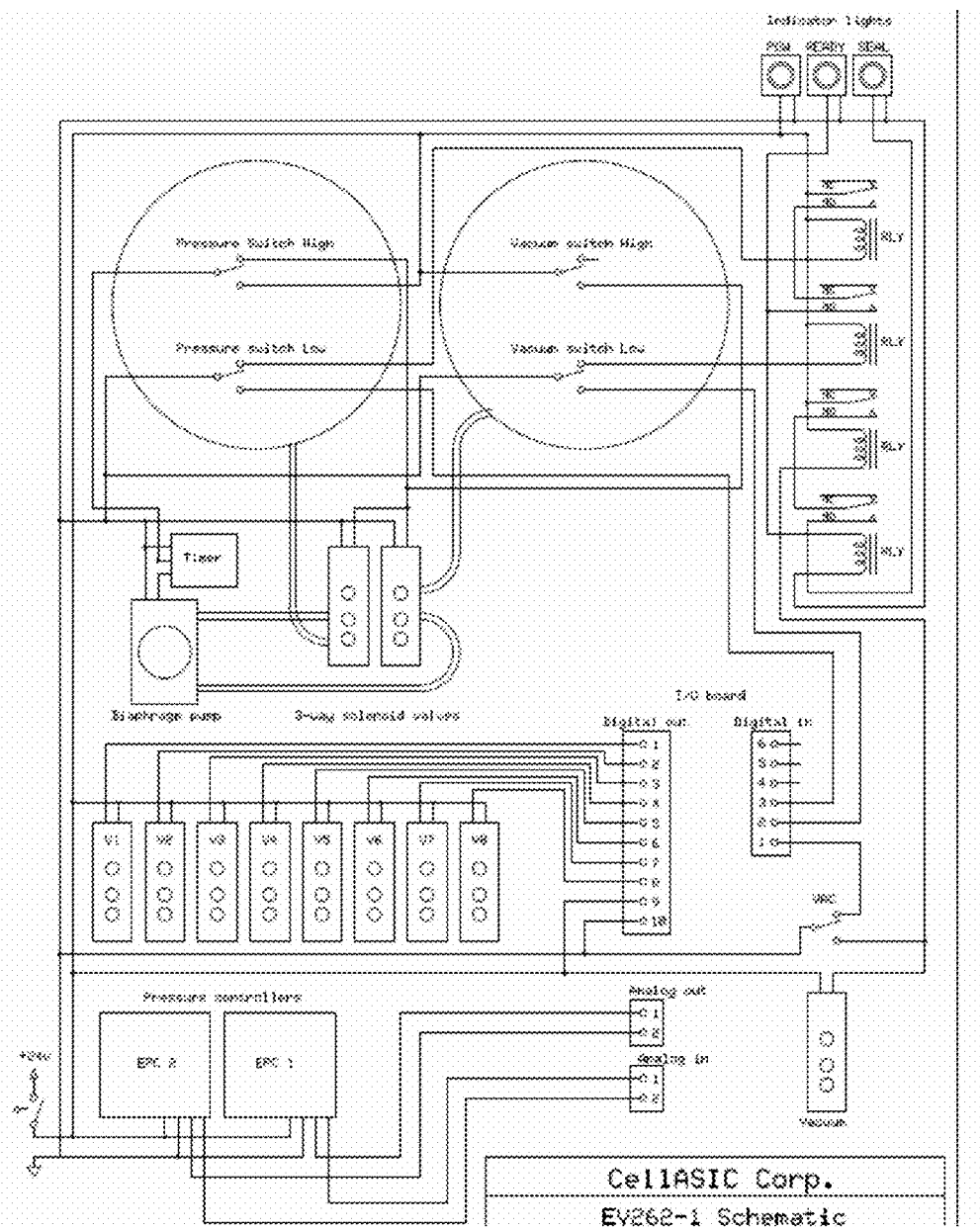
FIG. 20A-D are schematics of an example implementation of electronic control circuits for a manifold according to specific embodiments of the invention.
Figure 20B:
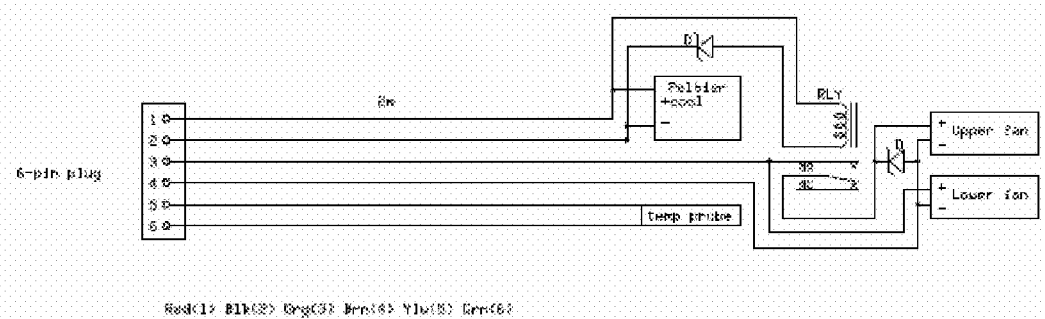
Figure 20C:
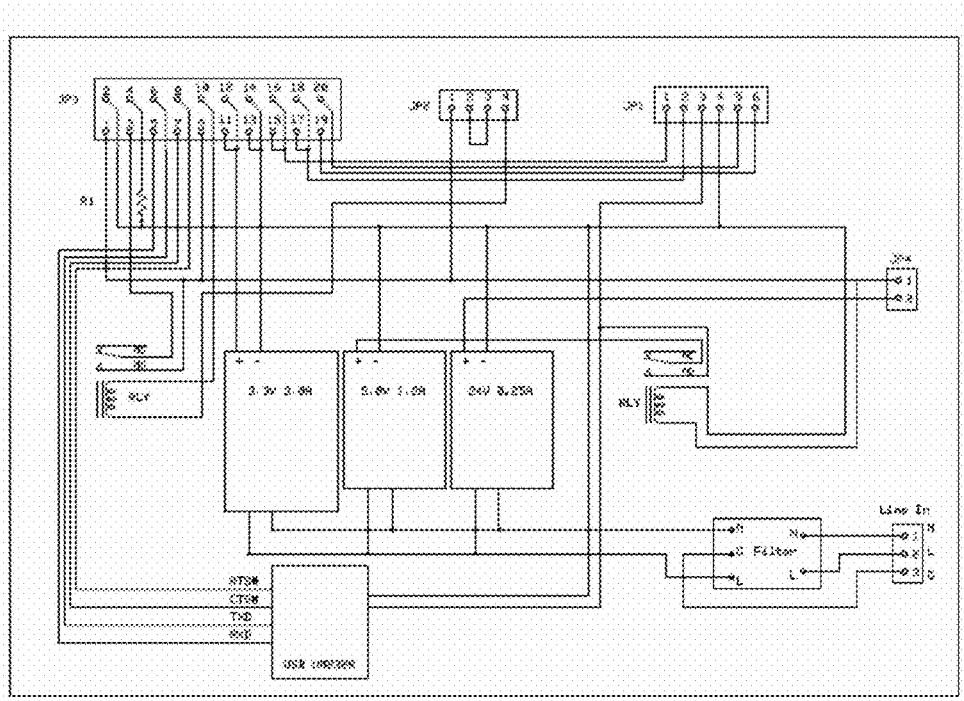
Figure 20D:
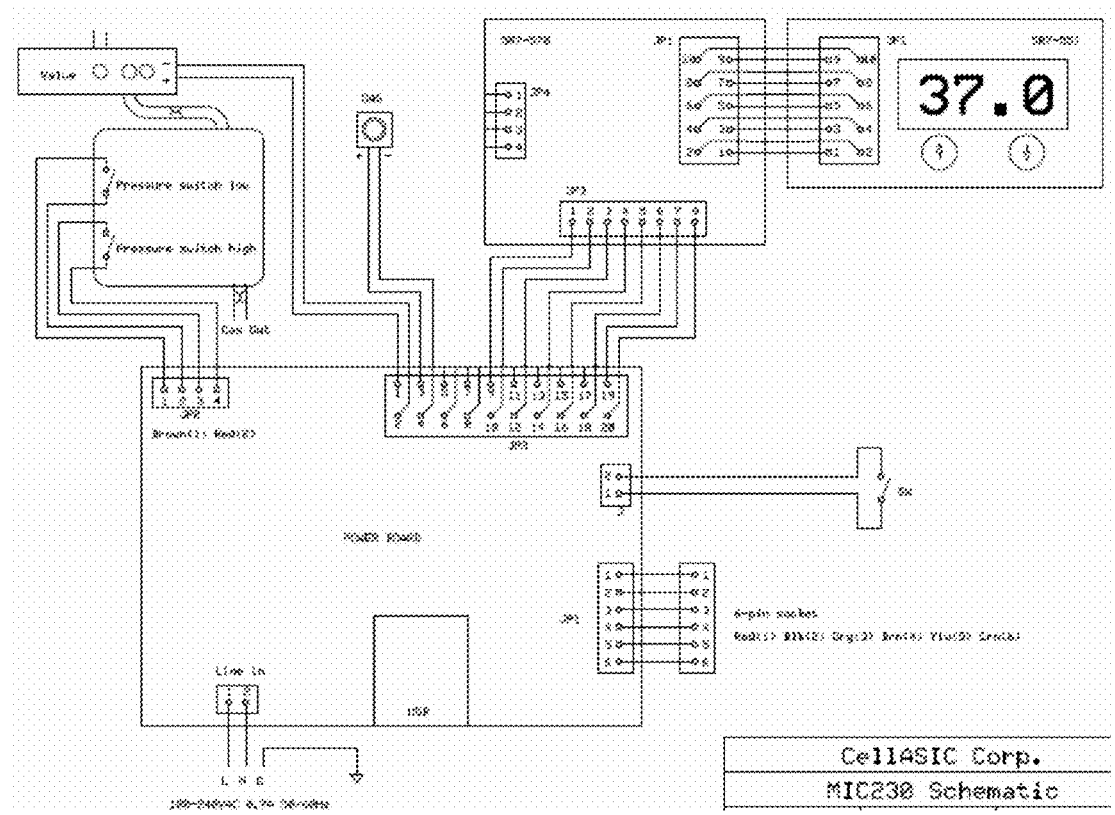

FIG. 18 is a block diagram showing an automated piston driven system according to specific embodiments of the invention. According to further specific embodiments, an auto-sealer somewhat similar to a plate reader commonly used in biotechnology with the main difference is the design of the system component to allow automated handling of the microfluidic plates. In this implementation, the positive seal between manifold and microfluidic plate is still accomplished by applying vacuum to the interstitial areas, but the necessary initial downward force is applied mechanically. The area above the manifold is clear to allow access by an automated liquid hander such as the Tecan EVO. Vacuum and pressure sensors as well as plate presence and carriage position sensors allow for intelligent software based error handling. FIG. 18B is an image sequence showing how the automatic sealing device accepts and seals the manifold to a microfluidic plate. A single pneumatic linear actuator (e.g., a piston) provides horizontal and vertical motion. It has been found that this single operation allows more precise control of the manifold and plate and holds the plate in place during operation of the pneumatic manifold.

Other Embodiments

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A microfluidic cell culture system comprising:
    at least one culture unit configured on a culture plate comprising:
        a microfluidic culture chamber;
        a perfusion barrier separating said microfluidic culture chamber from one or more medium flow channels;
        a plurality of independent inlet channels in fluid communication with said one or more medium flow channels;

and
   an outlet reservoir in fluid communication with said microfluidic culture chamber; and
a pneumatic manifold;
   wherein the culture plate is positively sealed to said pneumatic manifold, allowing pressure driven control of the plurality of independent inlet channels so that solutions can be quickly changed over the cells or can be multiplexed or combined in the microfluidic culture chamber;
   wherein said pneumatic manifold further comprises a heat exchange module for providing a circulating heat controlled gas in a contained gas volume over said microfluidic culture chamber.

2. The system of claim 1 wherein said perfusion barrier is used to reduce flow pressure from said inlet channels to said microfluidic culture chamber.

3. The system of claim 1 wherein said perfusion barrier is used to contain a gel media to said microfluidic culture chamber.

4. The system of claim 1 wherein said perfusion barrier mostly surrounds the microfluidic culture chamber to separate the microfluidic culture chamber from the one or more medium flow channels.

5. The system of claim 1, further comprising an automatic handling system for sealing the pneumatic manifold to the microfluidic culture plate comprising:
   a pneumatic linear actuator cylinder;
   one or more position sensors;
   two arms for holding the manifold from the sides, without blocking a view through the top of the manifold;
   a plate carriage and plate grippers for holding the culture plate;
   said system configured so that movement of the cylinder causes the plate carriage to move horizontally to a position under said manifold;
   said system configured so that movement of the cylinder causes the manifold to descend onto the plate.

6. The system of claim 5 further wherein: the cylinder is attached to the arms so that the cylinder provides both horizontal and vertical motion.

7. The system of claim 5 further wherein: said positive seal between the manifold and microfluidic culture plate is accomplished by applying vacuum through the manifold to the interstitial areas of the microfluidic culture plate while the necessary initial downward force is applied mechanically.

8. The microfluidic cell culture system of claim 1, further comprising a medium well in fluid communication with said one or more medium flow channels.

9. The microfluidic cell culture system of claim 8, wherein said medium well is a gravity perfusion well.

10. The microfluidic culture system of claim 1, further comprising a cell inlet in fluid communication with said culture chamber.

11. The microfluidic cell culture system of claim 1, further comprising a gas circulation region formed by the positive seal of said pneumatic manifold to said microfluidic culture plate.

12. The microfluidic cell culture system of claim 11 wherein said heat exchange module further comprises a fan to circulate gas within said gas circulation region.

13. The microfluidic cell culture system of claim 1, wherein said heat exchange module comprises a convective heat exchanger.

14. The microfluidic cell culture system of claim 13, wherein said convective heat exchanger comprises heat exchange fins.

15. The microfluidic cell culture system of claim 14, wherein said heat exchange module further comprises a fan to circulate air over said heat exchange fins.

16. The microfluidic cell culture system of claim 1, wherein said pneumatic manifold further comprises a gas input.

* * * * *